(12) United States Patent
Morihisa

(10) Patent No.: US 12,365,000 B2
(45) Date of Patent: Jul. 22, 2025

(54) SPRAYING APPARATUS

(71) Applicant: K.K. KUKAN JOKIN, Tokyo (JP)

(72) Inventor: Yasuhiko Morihisa, Tokyo (JP)

(73) Assignee: K.K. KUKAN JOKIN, Tokyo (JP)

( * ) Notice: Subject to any disclaimer, the term of this patent is extended or adjusted under 35 U.S.C. 154(b) by 167 days.

(21) Appl. No.: 17/911,413

(22) PCT Filed: Mar. 4, 2021

(86) PCT No.: PCT/JP2021/008364
§ 371 (c)(1),
(2) Date: Sep. 13, 2022

(87) PCT Pub. No.: WO2021/182274
PCT Pub. Date: Sep. 16, 2021

(65) Prior Publication Data
US 2023/0138209 A1 May 4, 2023

(30) Foreign Application Priority Data
Mar. 13, 2020 (JP) ................................. 2020-043630

(51) Int. Cl.
*B05B 17/06* (2006.01)
(52) U.S. Cl.
CPC ............................... *B05B 17/0615* (2013.01)
(58) Field of Classification Search
CPC ... B05B 7/0012; B05B 15/58; B05B 17/0669; B05B 17/0615; B05B 1/262; B05B 17/06; B05B 17/0638; B05B 17/0623; B05B 14/00; B05B 7/2429; B05B 7/262; A61L 2209/132; A61L 2209/234; A61L 2/22
See application file for complete search history.

(56) References Cited

U.S. PATENT DOCUMENTS 9,308,544 B2 * 4/2016 Ljuhar ...................... A61L 9/14
2013/0026250 A1 * 1/2013 Burt .................... B05B 17/0615
239/302

FOREIGN PATENT DOCUMENTS

| JP | S60-50728 U | 4/1985 |
|---|---|---|
| JP | H08-309248 A | 11/1996 |
| JP | 2004-216221 A | 8/2004 |
| JP | 2009-506850 | 2/2009 |
| JP | 3224953 U | 1/2020 |

* cited by examiner

*Primary Examiner* — Christopher R Dandridge
(74) *Attorney, Agent, or Firm* — j-pat U.S. Patent Legal Services; James W. Judge

(57) ABSTRACT

Spraying apparatus enabling large-volume generation of particles minute to a Brownian-motion engendering level. An atomization tank stores liquid formulation; an in-tank arrangement of ultrasonic vibration elements atomizes the liquid formulation to generate fine particles; a blower having a blower element for maintaining predetermined rpm blasts into the atomization tank interior through a top-panel blow port conveyance air conveying the fine particles; and a send-out port on the tank releases the fine particles together with the conveyance air. An in-tank baffle plate, situated above the ultrasonic vibration elements and underneath the blow port, is oriented to block liquid columns produced by the ultrasonic vibration elements, and conveyance air supplied through the blow port.

1 Claim, 20 Drawing Sheets

SPRAYING APPARATUS

TECHNICAL FIELD

Figure 1A:
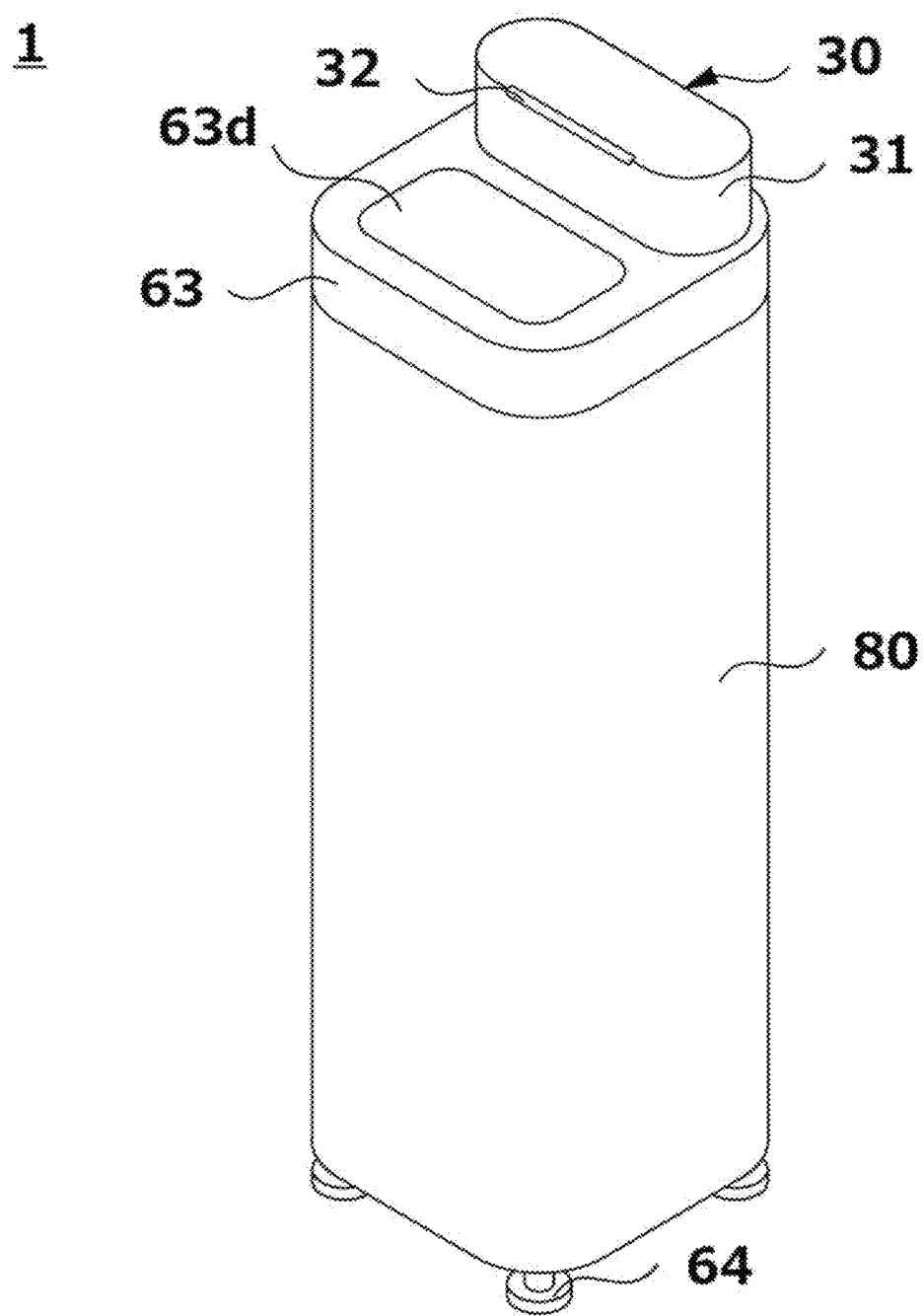

The present invention relates to technology for generating fine particles in a spraying device that sprays liquid into a space.

BACKGROUND ART

Various spraying devices that atomize and spray into a space water or aqueous solutions that exhibit predetermined effects have been developed.

In spraying devices of this kind, in order to uniformly and wide-rangingly diffuse fine particles inside a space, it is necessary to stably generate fine particles having a desired particle size—in particular, a particle size tiny to a level at which the fine particles can give rise to Brownian motion within air.

As an example of this sort of spraying device, there is the instance in which, e.g., in a broad space such as an elderly-facility assembly hall, or livestock shelter such as a cowshed, piggery, or poultry farm, the need arises to spray a large volume of a liquid formulation having a disinfecting action. In such instances, it is undesirable that the particle diameters be large, because the particles will fall to the floor or ground before reaching every nook and cranny of the space, and at the same time dampen the floor, walls, and skin, becoming the cause of slipping, of mold and mildew, and of colds. Therefore, in order that the particles float within the air for a long time such that the sterilizing effectiveness is demonstrated, it is necessary to generate fine particles having particle diameters tiny to a level that can give rise to Brownian motion.

In general, in order to atomize and spray a liquid, in an atomizing unit in which water or an aqueous solution is stored, technology is adopted in which a liquid column generated utilizing a vibrator such as an ultrasonic vibrator is impacted on a separator and separated into large liquid droplets and small mist droplets, and a conveyance medium supplied from a blower or the like is utilized to convey and diffuse into the air the mist droplets alone. (Patent Document 1, Patent Document 2)

PRECEDENT TECHNICAL LITERATURE

Patent Document(s)

Patent document 1: JP H8-309248 A
Patent Document 2: JP S60-50728 U

SUMMARY OF INVENTION

Issues Invention Is to Address

The technology disclosed in Patent Document 1 and Patent Document 2 affords a spray apparatus capable of selectively spraying mist droplets separated from liquid droplets. Nevertheless, with the technology disclosed in Patent Documents 1 and 2, because air is directly supplied to the region where the liquid column collides on the separator, due to the air the flow is disturbed, such that particles of relatively large particle diameter also get swept into and are conveyed on the air. Consequently, the particle diameter of fine particles conveyed on the air and sprayed is on the order of 10 µm, encumbering the generating of fine particles (particle size of about 0.1 to 2 µm) that are tiny to a level that can give rise to Brownian motion.

What is more, in order to evenly spread fine particles over a broad space, it is necessary to supply a large volume of conveyance air for conveying the fine particles, meaning that in such cases not only fine particles of tiny diameter but also particles whose diameter is large are conveyed, making difficult the conveying of only fine particles that are tiny to a level that can give rise to Brownian motion.

Generating/conveying only tiny fine particles necessitates controlling with high precision the voltage applied to the vibrator and the rpm of the delivery machine at the same time, which without specialized knowledge is challenging.

An object of the present invention, brought about taking these sorts of issues into consideration, is to make available a spraying apparatus capable of generating a large volume of fine particles having particle diameters minute to a level that stably can give rise to Brownian motion, even without complex control employing expensive control devices.

Means for Resolving Issues

With the present invention, the following sort of resolution means are made available.

The invention involving a first characteristic affords a spraying apparatus provided with: an atomization tank enabled for storing a liquid formulation; an atomizing device being ultrasound vibrating elements arranged in the atomization tank interior, for atomizing the liquid formulation to generate fine particles; a blower furnished with a blowing element enabled for maintaining predetermined rpm, for blasting into the atomization tank interior, through a blow port provided in a top panel of the atomization tank, conveyance air that is for conveying the fine particles of the liquid formulation; a send-out port, provided in the atomization tank, through which the fine particles are sent out together with the conveyance air; and a first baffle plate arranged in the atomization tank interior so as to receive liquid columns of the liquid formulation, generated by the ultrasonic vibration elements; wherein the baffle plate is furnished with an edge part arranged directed toward one widthwise end of the atomization tank and meanwhile arranged in the atomization tank spaced apart at a predetermined spacing from a lateral surface along the one widthwise end and directed at the lateral surface, and with a connection part connected to an inner side of a top panel of the atomization tank; the baffle plate is disposed above the ultrasonic vibration elements, and underneath the blow port, in an orientation blocking liquid columns produced by the ultrasonic vibration elements, and conveyance air blasted through the blow port by the blower; and the blow port and the send-out port are provided on an inner surface of the atomization tank and in locations on opposites sides from each other, with the connection part put in between.

According to the invention involving the first characteristic, thanks to having a configuration in which conveyance air that is for conveying the fine particles of the liquid formulation is blasted into the atomization tank interior, through a blow port provided in a top panel of the atomization tank, a configuration in which the baffle plate is arranged directed toward one widthwise end of the atomization tank and meanwhile furnished with a connection part connected with a top panel of the atomization tank, and a configuration in which the baffle plate is disposed underneath the blow port, in an orientation where it blocks conveyance air blasted through the blow port by the blower, roughly the entire amount of conveyance air blown in, by the operation of the blower, through the blow port provided in the top panel of the atomization tank supplied directed at the baffle plate disposed underneath the blower port.

Then, because the baffle plate has a configuration in which it is furnished with an edge part disposed spaced apart at a predetermined spacing from a lateral surface along one widthwise end of the atomization tank and directed at the lateral surface, conveyance air supplied to head toward the baffle plate passes through a gap formed between the edge part and the lateral surface. At that point, because the edge part is disposed spaced apart at a predetermined spacing from and directed at the lateral surface of the atomization tank, in the passing of the blower-supplied conveyance air through the gap between the edge part and the lateral surface, a one-time constricted flow arises, such that after passing through the gap the conveyance air expands.

Figure 1B:
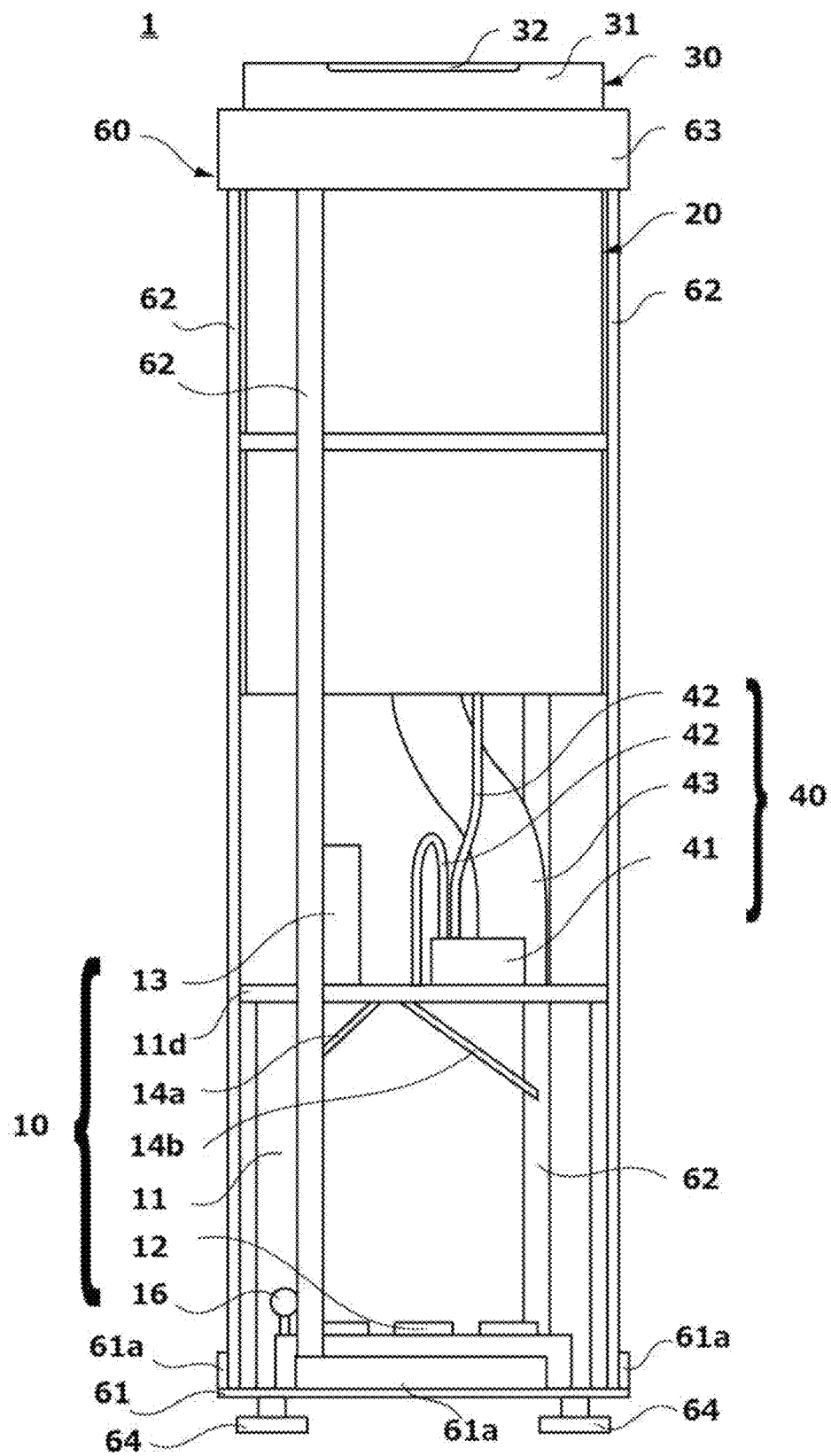
Figure 1C:
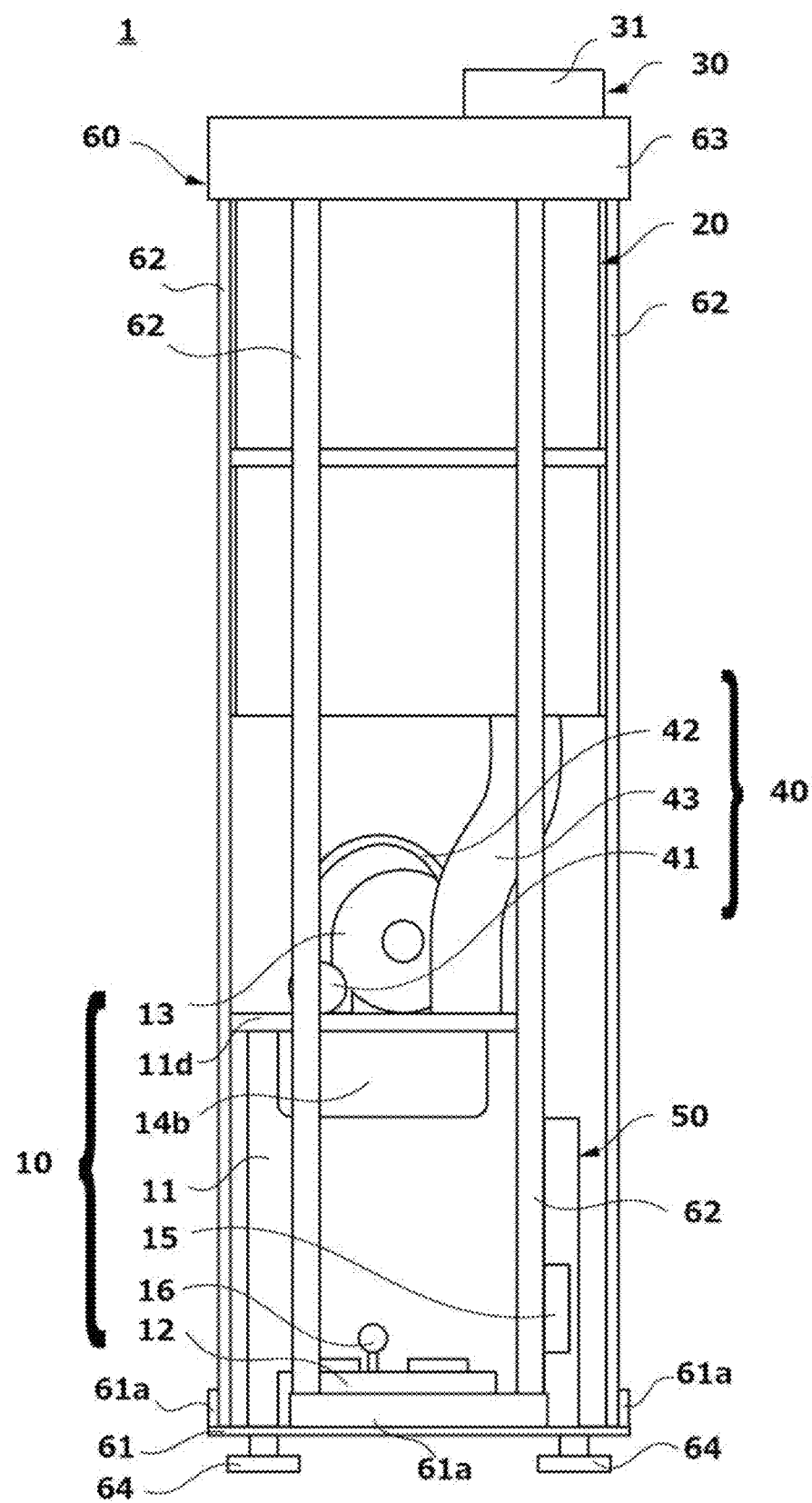
Figure 1D:
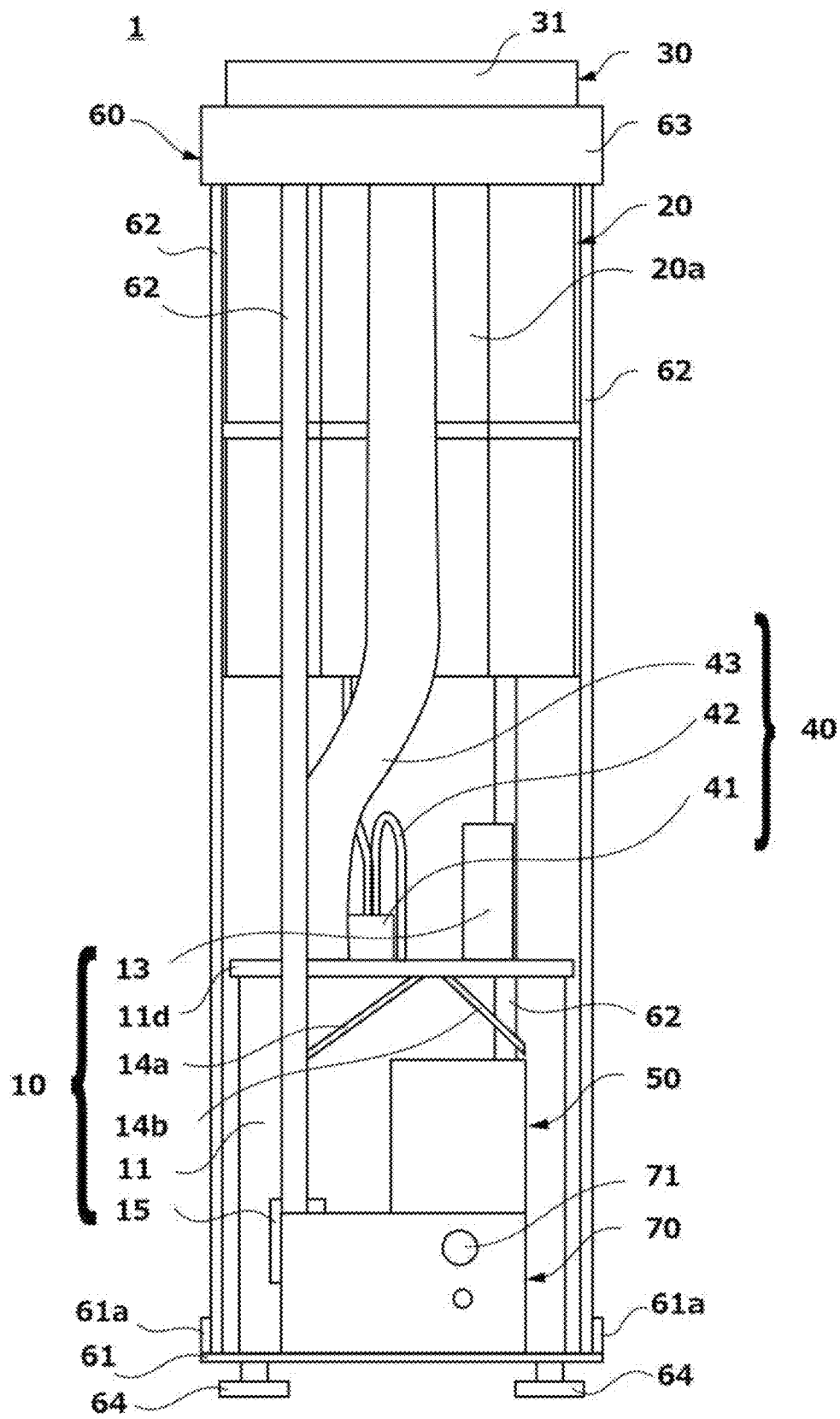

Furthermore, because it has a configuration in which the blow port and the send-out port are provided on an inner surface of the atomization tank and in locations on opposites sides from each other, with the connection part put in between, conveyance air having passed through the gap between the edge part and the lateral surface passes along the lower surface of the baffle plate and flows toward the send-out port. Therein, the conveyance air conveys only fine particles that float along the lower surface of the baffle plate.

In that situation, as described above, the fact that when conveyance air supplied from the blower passes through the gap between the edge part and the lateral surface a one-time constricted flow arises, such that the conveyance air expands after passing through the gap, means that in the post-gap-passing region—that is, in the vicinity of the undersurface of the baffle plate for receiving liquid columns of the liquid formulation—a pressure loss is produced. On account of the pressure of the conveyance air dropping still further in that negative-pressure region, particles other than fine particles that are of extraordinarily tiny particle diameter cannot be conveyed, leaving them to fall to the liquid surface below. The result is that only fine particles whose particle diameters are tiny to a level that can give rise to Brownian motion can be conveyed toward the send-out port by the conveyance air.

Here, because the baffle plate has a configuration in which, above the ultrasonic vibration elements and underneath the blower, it is disposed in an orientation where it blocks liquid columns produced by the ultrasonic vibration elements, and conveyance air blasted through the blow port by the blower, the particles can be reliably selected with no direct interfering between the liquid columns, and the conveyance air blasted into the atomization tank interior by the blower. That is, supposing the conveyance air that is supplied directed downward, and the liquid columns that gush out directed upward directly interfered with each other, the mutual flow would be disturbed, harming the particle-selection capacity, making it impossible to convey solely the fine particles. With the invention involving the first characteristic, however, the fact that the baffle plate, underneath the blow port and above the ultrasonic vibration elements, is disposed in an orientation where it blocks the liquid columns produced by the ultrasonic vibration elements and the conveyance air blasted through the blow port by the blower, makes it possible to prevent the conveyance air and the liquid columns from directly interfering, with the result that with the conveyance air and liquid columns not disturbing each other's flows, selecting of particles can be reliably carried out, leaving only fine particles that are tiny to a level that can give rise to Brownian motion able to be conveyed.

Effect of the Invention

According to the present invention, a spraying apparatus that, even for persons for whom the job is unfamiliar, is capable of generating a large volume of fine particles having particle diameters minute to a level that stably can give rise to Brownian motion, even without complex control employing expensive control devices, may be made available.

BRIEF DESCRIPTION OF DRAWINGS

FIG. 1A is a perspective view of a spraying apparatus 1 involving a core embodying mode.

FIG. 1B is an elevational view of the spraying apparatus 1 involving the core embodying mode, with its cover member 80 having been removed.

FIG. 1C is a right lateral side view of the spraying apparatus 1 involving the core embodying mode, with its cover member 80 having been removed.

FIG. 1D is a rear side view of the spraying apparatus 1 involving the core embodying mode, with its cover member 80 having been removed.

FIG. 2A is a partially enlarged perspective view of an atomization unit 10 involving the core embodying mode.

FIG. 2B is a schematic view of the atomization unit 10 involving the core embodying mode, in a state during use.

FIG. 3A is a perspective view of a spouting unit 30 for the spraying apparatus 1 involving the core embodying mode.

FIG. 3B is a plan view of the spouting unit 30 for the spraying apparatus 1 involving the core embodying mode.

FIG. 3C is an elevational view of the spouting unit 30 for the spraying apparatus 1 involving the core embodying mode.

FIG. 3D is a bottom-face view of the spouting unit 30 for the spraying apparatus 1 involving the core embodying mode.

FIG. 4A is an elevational view of a mounting unit 60 involving the core embodying mode.

FIG. 4B is a cross-sectional view along A-A in FIG. 4A.

FIG. 4C is a bottom-face view of a base component 61 involving the core embodying mode.

FIG. 5A is a plan view of a top component 63 involving the core embodying mode, in a state in which a top-component cover 63*g* has been removed.

FIG. 5B is a cross-sectional view along A-A in FIG. 5A.

FIG. 5C is a bottom-face view of the top component 63 involving the core embodying mode.

FIG. 5D is a plan view of the top-component cover 63*g* involving the core embodying mode.

FIG. 5E is a perspective view of the top component 63 and the spouting unit 30 during liquid-formulation replenishment.

FIG. 6 is a flowchart of a liquid-formulation spraying method employing an spraying apparatus 1 involving the core embodying mode.

FIG. 7A is a schematic view of an atomization unit 10 involving Modification Example 2, in a state during use.

FIG. 7B is a schematic view of an atomization unit 10 involving Modification Example 3, in a state during use.

FIG. 7C is a schematic view of the atomization unit 10 involving Modification Example 3, in a state during use.

FIG. 7D is a schematic view of the atomization unit 10 involving Modification Example 3, in a state during use.

MODE(S) FOR IMPLEMENTING INVENTION

Hereinafter, modes for implementing the present invention will be described with reference to the drawings. It should be noted that this is just an example, and the technical scope of the present invention is not limited to this.

Overall Configuration of Spray Apparatus With reference to FIG. 1A-1D, the overall configuration of spraying device 1 according to the present embodying mode will be described. FIG. 1A shows a perspective view, FIG. 1B shows a front view with a cover member 80 removed, FIG. 1C shows a right-side view with the cover member 80 removed, and FIG. 1D shows a rear view with the cover member 80 removed. It should be noted that in FIG. 1B, illustration of a liquid level sensor 15, a control unit 50, and a power supply unit 70 is omitted, and in FIG. 1C, illustration of the power supply unit 70 is omitted.

As illustrated in FIGS. 1A to 1D, the spraying apparatus 1 of the present embodying mode is constituted by: an atomizing unit 10 that atomizes a liquid formulation to generate and convey fine particles; a tank unit 20 that stores a liquid formulation to be supplied to the atomizing unit; a spouting unit 30 that spouts the fine particles generated by the atomizing unit 10; a supply unit 40 that sends out the fine particles generated in the atomizing unit 10 and supplies the liquid formulation to the atomizing unit 10; a control unit 50 that controls instruments; an mounting unit 60 that fixes each unit together; a power supply unit 70 that supplies power to each instrument; and a cover member 80 that covers each unit.

In addition, in the present embodying mode, it is assumed that a chlorous acid aqueous solution having a sterilizing effect is used as the liquid formulation, and the spraying apparatus 1 is used as a sterilizing device that kills viruses and bacteria floating in the air.

Configuration of Atomizing Unit 10

With reference to FIGS. 1 and 2, the atomizing unit 10 according to the present embodying mode will be described. FIG. 2A shows a partially-enlarged perspective view of the atomizing unit 10, and FIG. 2B is a schematic diagram illustrating how the atomizing unit 10 is used.

As illustrated in FIG. 2A, the atomizing unit 10 includes an atomization tank 11 having a predetermined width, enabled for storing a liquid formulation; an atomizing device 12 being ultrasonic vibrators 12*a*, 12*b*, 12*c* . . . plurally arranged widthwise and depthwise in the atomization tank 11 interior, for atomizing the liquid formulation to produce fine particles; a blower 13 furnished with a blowing element, not illustrated, enabled for maintaining predetermined rpm, for blasting into the atomization tank 11 interior, through a blow port 11*b* provided in the atomization tank 11, conveyance air that is for conveying the fine particles of the liquid formulation; two baffle plates 14*a* and 14*b* arranged so as to receive liquid columns of the liquid formulation, produced by the ultrasonic vibrators 12*a*, 12*b*, 12*c* . . . ; and a liquid level sensor 15 for detecting a liquid level in the atomization tank 11.

The atomization tank 11 is for storing and atomizing the liquid formulation supplied from the tank unit 20, and has a substantially rectangular parallelepiped shape having a predetermined width. In the top panel 11*d* of the atomization tank 11, a supply port 11*a* is formed; through the supply port 11*a*, the liquid formulation supplied from the tank unit 20 through the liquid-formulation supply pump 41 of the later-described supply unit 40 flows into the atomization tank 11 interior. In addition, in the top panel 11*d* of the atomization tank 11, a blow port 11*b* is formed; through the blow port 11*b*, the conveyance air from the blower 13 flows into the atomization tank 11 interior. Furthermore, in the top panel 11*d* of the atomization tank 11, a send-out port 11*c* is formed; through the send-out port 11*c*, the fine particles atomized in the atomization tank 11 is sent out along with the conveyance air. The atomization tank 11 is fixed to a lower-part base 61 of the later-described mounting unit 60 by known means such as screw-fastening. In this situation, the atomization tank 11 is arranged inside the region defined by six columnar members 62 of the mounting unit 60. The atomization tank 11 is made of polyethylene terephthalate (PET). In addition, in the present embodying mode, the top panel 11*d* of the atomization tank 11 is formed of a top panel piece attached to the main body of the atomization tank 11.

The atomizing device 12, being a device equipped with a plurality of ultrasonic vibrators 12*a*, 12*b*, 12*c* . . . arranged at the bottom inside the atomization tank 11, is operated by the power supplied from the power supply unit 70 to emit ultrasonic waves. The atomizing device 12 according to the present embodying mode, in which ultrasonic vibrators 12*a*, 12*b*, 12*c*, 12*d*, 12*e*, and 12*f* are arranged in a plane in two rows along the depth and in three rows along the width of the atomization tank 11, atomizes the liquid formulation wide-rangingly in the atomization tank 11 wide-rangingly to produce fine particles. When the atomizing device 12 is operated, from the liquid surface, for each of the arranged ultrasonic vibrators 12*a*, 12*b*, 12*c* . . . , a liquid column is produced upward from each of the ultrasonic vibrators 12*a*, 12*b*, 12*c* . . . .

The blower 13, furnished with a blowing element not illustrated whose rpm can be controlled according to a signal from the control unit 50, is for supplying conveyance air for conveying the atomized liquid formulation through the blow port 11*b* into the atomization tank 11 interior, and a blast port, not illustrated, for blasting the conveyance air is connected to the blow port 11*b* of the atomization tank 11, arranged so as to be able to blow air downward. In the present embodying mode, the blower 13, driven by power supplied from the power supply unit 70, is rpm-controlled by changing the applied voltage according to a signal from the control unit 50.

Next, the two baffle plates 14*a* and 14*b* will be described. The baffle plates 14*a* and 14*b* are flat pieces formed of stainless steel, and their basic function is to separate the liquid droplets produced by the ultrasonic vibration of the atomizing device 12 into large liquid droplets and tiny fine particles. That is, when a liquid column is produced above each of the ultrasonic vibrators 12*a*, 12*b*, 12*c* . . . , liquid droplets of large particle diameter contained in the liquid column collide on the baffle plates 14*a* and 14*b*, and flow downward and then back to the liquid layer stored in the atomization tank 11. On the other hand, mist droplets of small particle diameter contained in the liquid column float in the vicinity of the baffle plates 14*a* and 14*b*, and are conveyed to the send-out port 11*c* by the conveyance air supplied by the blower 13. In this manner, by the action of the baffle plates 14*a* and 14*b*, the liquid droplets of large particle diameter and the mist droplets of small particle diameter produced by ultrasonic vibration can be separated.

In addition to this basic function, the baffle plates 14*a* and 14*b* according to the present embodying mode are arranged as follows so as to exhibit further function described below.

The baffle plate 14*a* according to the present embodying mode (first baffle plate in the present invention) is arranged below the blow port 11*b* and above the ultrasonic vibrators 12*a* and 12*d* arranged along one widthwise end of the atomization tank 11 among the ultrasonic vibrators.

In addition, the baffle plate 14*a* is arranged to incline downward toward the one widthwise end of the atomization tank 11, in such a manner that one end has a connection part 14*ac* (first connection portion in the present invention) connected to the top panel 11*d* of the atomization tank 11, and the other end has an edge part 14*ae* (first edge portion in the present invention) arranged spaced apart at a predetermined spacing from the lateral surface along one widthwise end of the atomization tank 11.

The baffle plate 14b (second baffle plate in the present invention) is arranged below the supply port 11a and the send-out port 11c and above the ultrasonic vibrators 12c and 12f arranged along the other widthwise end of the atomization tank 11 among the ultrasonic vibrators.

In addition, the baffle plate 14b is arranged inclined diagonally downward, toward the opposite side from the baffle plate 14a, that is, toward the other widthwise end of the atomization tank 11, in such a manner that one end has a connection part 14bc (second connection portion in the present invention) connected to the top panel of the atomization tank 11, and the other end has an edge part 14be (second edge portion of the present invention) arranged spaced apart at a predetermined spacing from the lateral surface along the other widthwise end of the atomization tank 11, that is, on the side opposite from the side where the baffle plate 14a is arranged.

In other words, the end part of the baffle plate 14a is arranged spaced apart at a predetermined spacing from the lateral surface along one widthwise end of the atomization tank 11, while the end part of the baffle plate 14b is arranged spaced apart at a predetermined spacing from the lateral surface along the other widthwise end of the atomization tank 11.

The blow port 11b is provided to one widthwise end of the connection part 14ac of the baffle plate 14a, and the send-out port 11c is provided to the other widthwise end of the connection part 14bc of the baffle plate 14b.

The liquid-level sensor 15 is for detecting liquid level in the liquid formulation stored in the atomization tank 11 interior, and in the present embodying mode, a float sensor arranged in the external part of the atomization tank 11 is employed. In this case, the atomization tank 11 is provided with a flow through-hole, not illustrated, at an appropriate height, and the liquid formulation flows into the liquid-level sensor 15 via the flow through-hole. Since the atomization tank 11 and the liquid-level sensor 15 connected via the flow through-hole are under the same pressure, the liquid level in the liquid-level sensor 15 and the liquid level in the atomization tank 11 have the same value. In this manner, the liquid level in the atomization tank 11 is detected by the external liquid-level sensor 15, but the sensor is not limited to this as long as the liquid level can be measured. The liquid-level sensor 15 in the present embodying mode is employed to detect a predetermined first liquid level h1 and a second liquid level h2 higher than the first liquid level h1.

The halt sensor 16 is, like the liquid-level sensor 15, for detecting the liquid level of the liquid formulation stored in the atomization tank 11 interior, but as later-described, is for detecting a liquid level for determining to forcibly halt the operation of the spraying apparatus 1.

As described above, the atomization tank 11 is arranged inside the region defined by the six columnar members 62 of the mounting unit 60, and also in the same manner, each instrument constituting the atomizing unit 10 is arranged inside the region defined by the six columnar members 62. In other words, when viewed in plan, the plurality of columnar members 62 is positioned outermost, and in the inner side of the region surrounded by the plurality of columnar members 62, each instrument is arranged to be positioned.

Configuration of Tank Unit 20

The tank unit 20 is for temporarily storing the liquid formulation to be supplied to the atomization tank 11 and is disposed above the atomizing unit 10. The tank unit 20 has a substantially rectangular parallelepiped shape, and has open on its upper surface an inflow port communicating with a liquid-formulation replenishing port 63e of a later-described top member 63. In addition, open on its bottom surface is a connection port connected to a liquid-formulation supply tube 42 of the supply unit 40. The tank unit 20 is fixed to the columnar members 62 by known means such as screw-fastening so as to be arranged inside the region defined by six columnar members 62 of the later-described mounting unit 60. In this situation, a flange part may be provided on the outer face of the tank unit 20, so that the flange part establishes connection to the columnar members 62. Substantially at the center of the tank unit 20, vertically formed is a recess 20a, which is configured such that a supply pipe 43 that supplies the fine particles and the conveyance air from the atomization tank 11 to the spouting unit 30 can pass through this recess 20a. The capacity of the tank unit 20 is larger than the capacity of the atomization tank 11, which enables a single replenishment of the liquid formulation to the tank unit 20 to supply the liquid formulation to the atomization tank 11 multiple times, thereby making it possible to continue operation over a long time. The tank unit 20 is formed of polyethylene terephthalate (PET), like the atomization tank 11.

Configuration of Spouting Unit 30

Figure 3A:
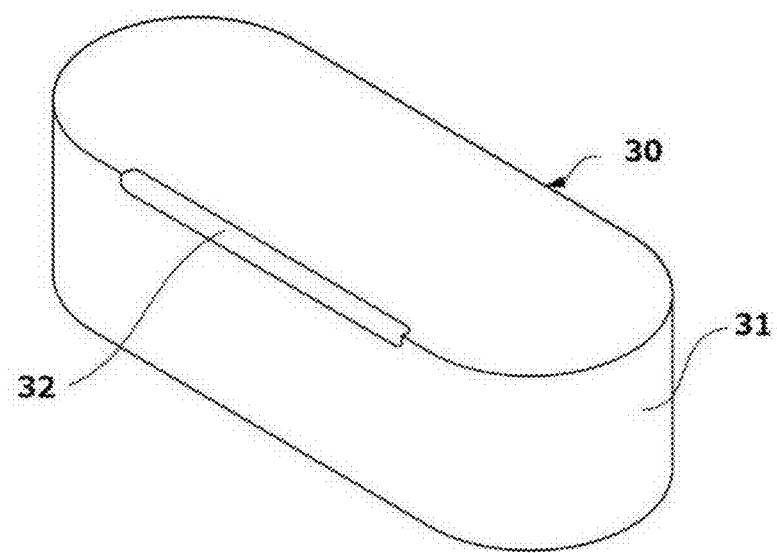
Figure 3B:
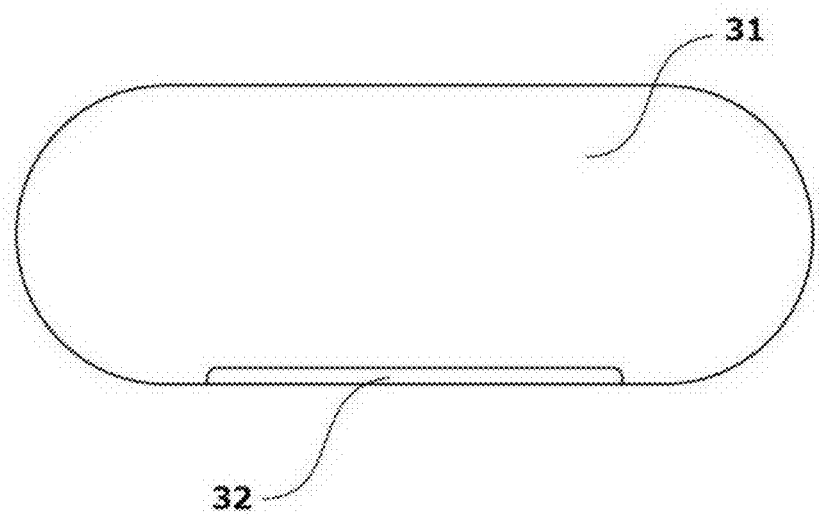
Figure 3C:
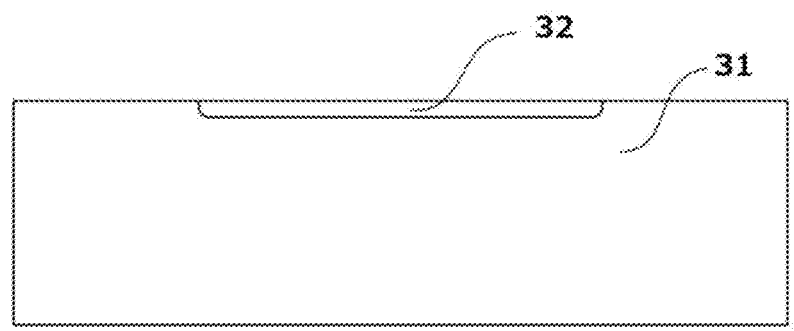
Figure 3D:
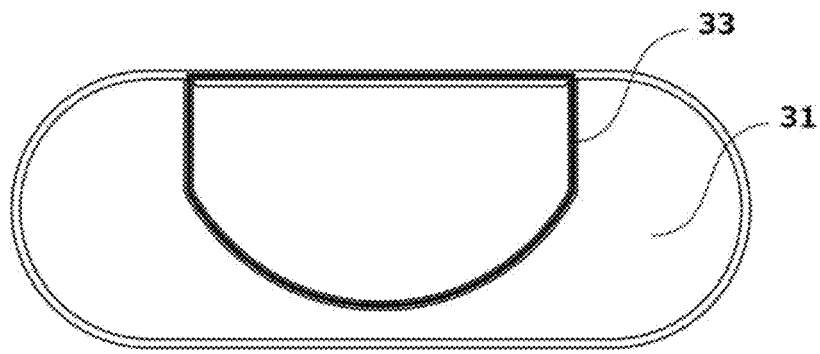

With reference to FIG. 3A-3D, the spouting unit 30 will be described. FIG. 3A shows a perspective view of the spouting unit 30, FIG. 3B a plan view of the spouting unit 30, FIG. 3C a front view of the spouting unit 30, and FIG. 3D a bottom view of the spouting unit 30.

The spouting unit 30 is for spouting the fine particles generated in the atomizing unit 10 together with the conveyance air, and is installed so as to protrude upward from the top member 63 arranged at the top of the mounting unit 60. The spouting unit 30, being formed of a bottomless, substantially cylindrical spouting element 31 having a predetermined width, depth, and height, has on its upper end a spray port 32 that inclines diagonally upward and is formed in the form of a slit widthwise. On the lower end of the spouting element 31, a plurality of lock hooks, not illustrated, that can be inserted into a locking recess 63b of the later-described top member 63, are formed.

Figure 5A:
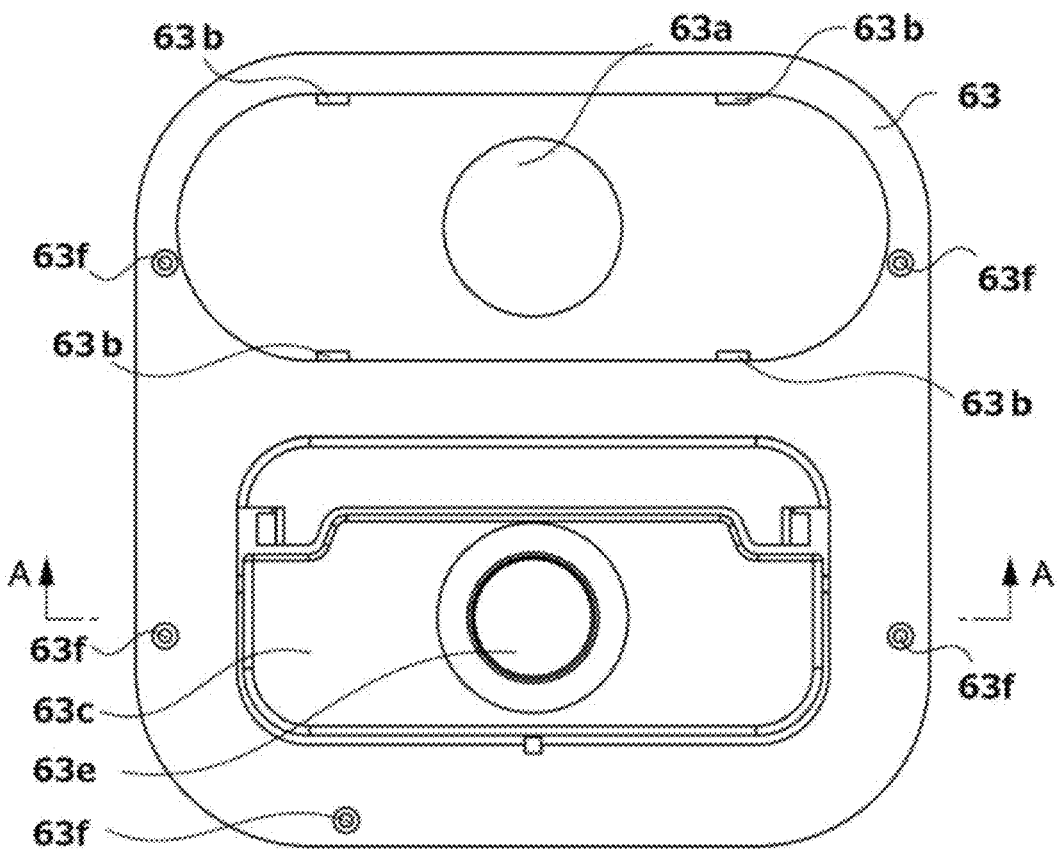

Inside the spouting element 31, a partition wall 33 is provided protruding from the inner side of the top panel, and by connecting of the supply pipe 43 of the supply unit 40 to the region surrounded by the partition wall 33, fine particles and conveyance air from the atomizing unit 10 flow into the spouting unit 30 interior. In this regard, description is made with reference to a plan view illustrating a state in which a top member cover 63g of the top member 63 illustrated in FIG. 5A is removed. In the top panel of the top member 63, a connection port 63a connected to the supply pipe 43 of the supply unit 40 opens. At the same time, in the top panel of the top member 63, the locking recess 63b to be locked to the locking hook, not illustrated, formed on the lower end part of the spouting unit 30, is formed. Then, when the locking hook of the spouting unit 30 is locked to the locking recess 63b of the top member 63, the lower end of the partition wall 33 seals and adheres to the periphery of the connection port 63a in the top member 63, and the interior region of the partition wall 33 and the supply pipe 43 of the supply unit 40 are connected via the connection port 63a.

On the upper end of the interior region of the partition wall 33, the spray port 32 in the form of a slit inclined diagonally upward is formed, and the fine particles and the conveyance air that has flowed into the interior region of the partition wall 33 through the connection port 63a are sprayed through the spray port 32.

Configuration of Supply Unit 40

With reference to FIG. 1A-1D again, the configuration of the supply unit 40 will be described.

As illustrated in FIGS. 1B to 1D, the supply unit 40 is constituted by the liquid-formulation supply pump 41 for supplying the liquid formulation stored in the tank unit 20 to the atomizing unit 10; the liquid-formulation supply tube 42 that is connected to the liquid-formulation supply pump 41 and circulates the liquid formulation between the tank unit 20 and the atomizing unit 10; and the supply pipe 43 supplies the fine particles generated in the atomizing unit 10 and the conveyance air to a spraying unit.

The liquid-formulation supply tube 42 connects a connection port, not illustrated, and the inlet of the liquid-formulation supply pump 41 formed in the bottom surface of the tank unit 20, and also connects the outlet of the liquid-formulation supply pump 41 and the supply port 11a formed in the top panel of the atomization tank 11.

In other words, by utilizing the liquid-formulation supply pump 41 and the liquid-formulation supply tube 42, the liquid formulation stored in the tank unit 20 can be supplied into the atomization tank 11 interior through the supply port 11a as needed.

In the present embodying mode, a tube pump is employed as the liquid-formulation supply pump 41, but the present invention is not limited to this.

The supply pipe 43 connects the send-out port 11c formed in the top panel of the atomization tank 11 and the connection port 63a of the top member 63.

In other words, the fine particles generated in the atomization tank 11 are send out through the send-out port 11c together with the conveyance air, circulate in the supply pipe 43 and through the connection port 63a of the top member 63, flow into the interior region of the partition wall 33 formed in the spouting unit 30, and sprayed through the spray port 32.

In the present embodying mode, the supply pipe 43 is constituted by an accordion-fold flexible tube, but is not limited to this. In addition, the supply pipe 43 passes through a vertical recess formed substantially at the center of the tank unit 20, and connects the send-out port 11c and the connection port 63a.

Configuration of Control Unit 50

The control unit 50 is for controlling driving of the blower 13 and the driving of the liquid-formulation supply pump 41, and is constituted by known circuits, switches, or the like.

Configuration of Mounting Unit 60

Figure 4A:
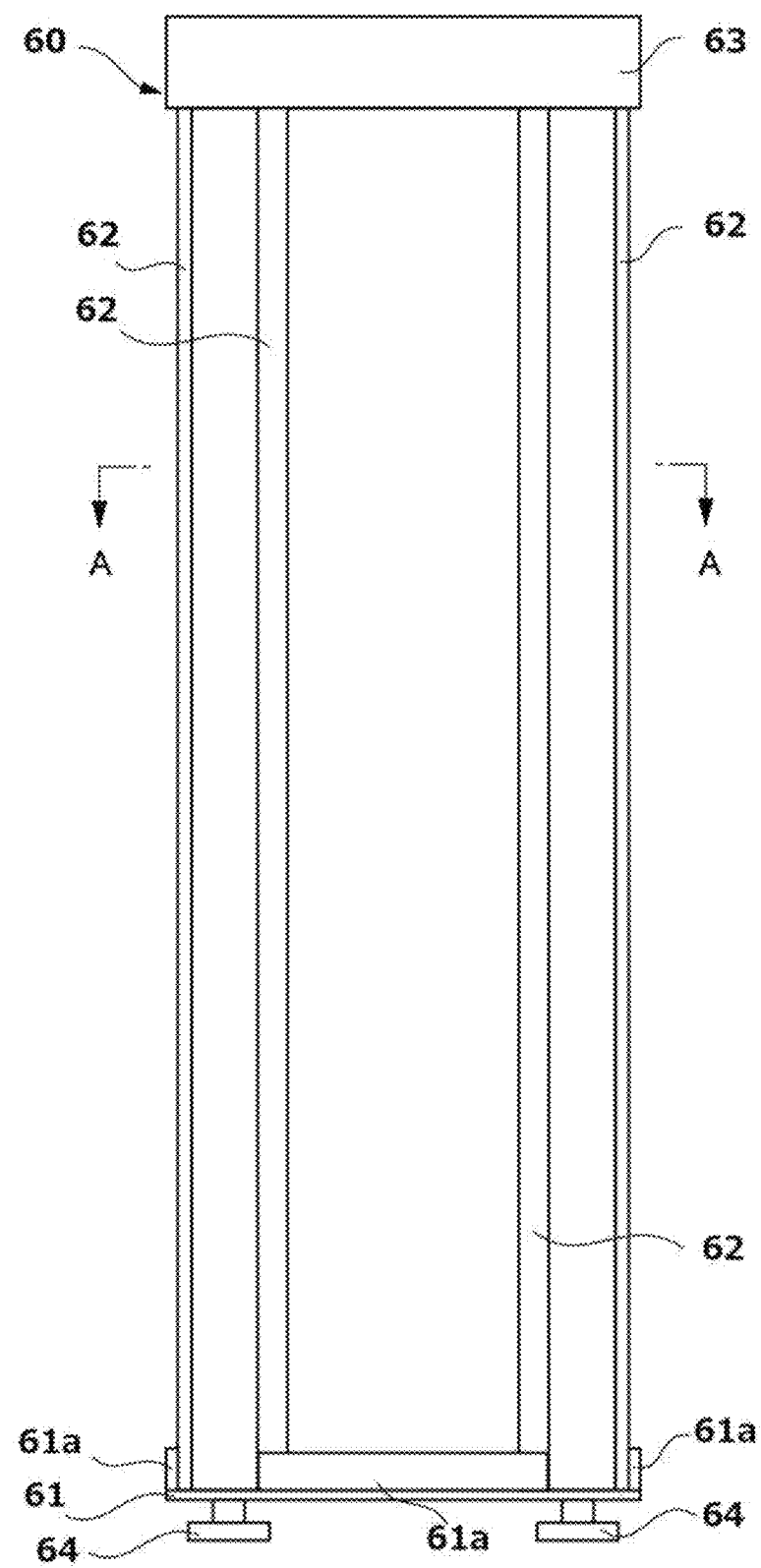
Figure 4B:
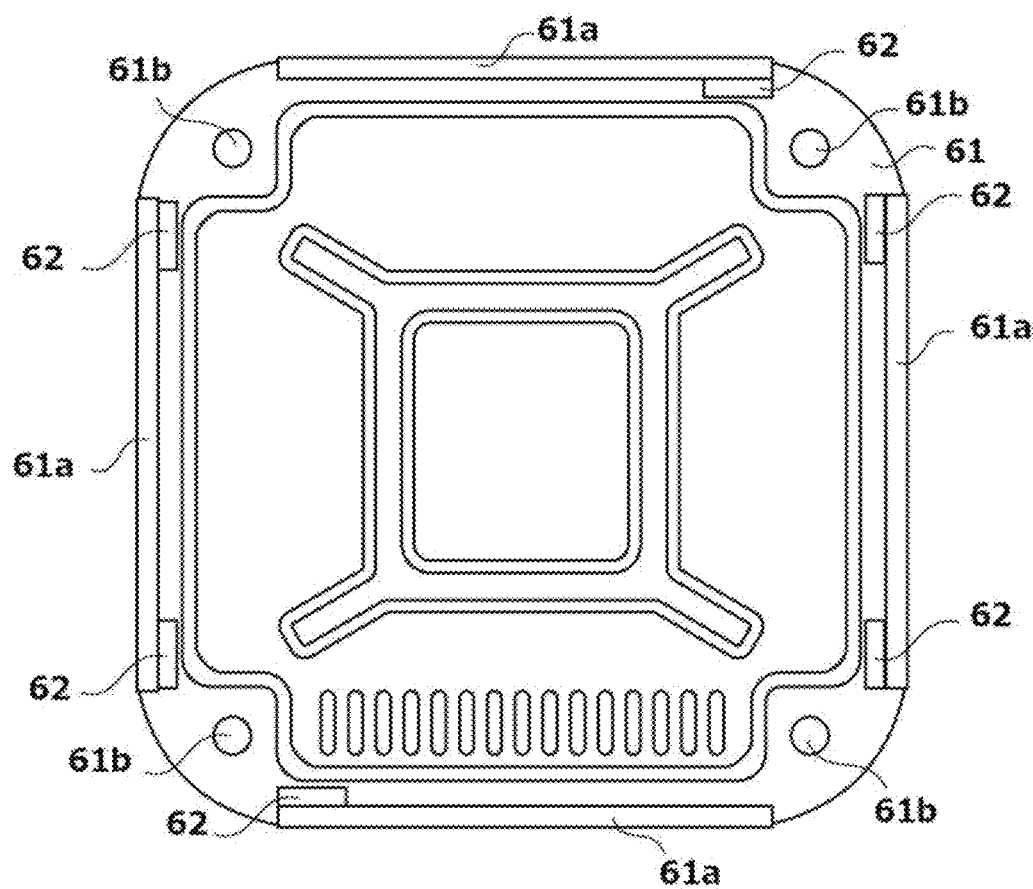
Figure 4C:
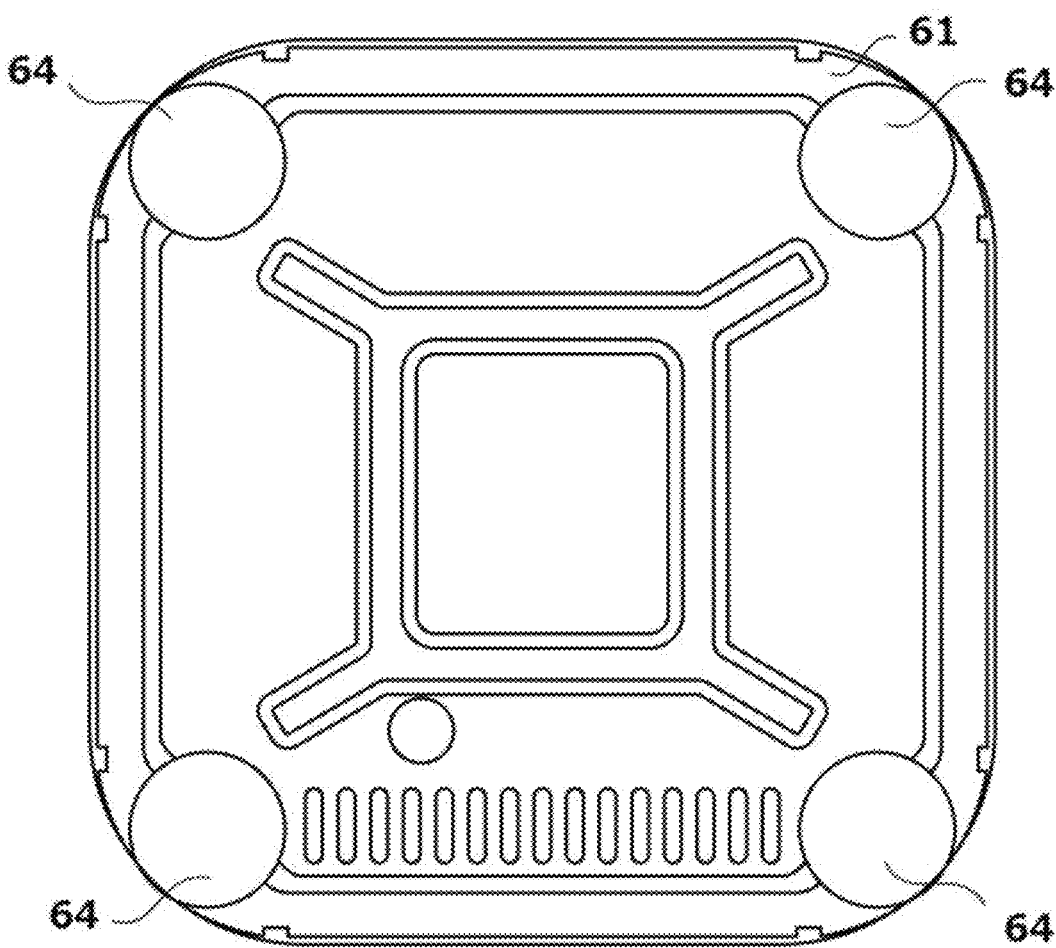

With reference to FIG. 4A-4C, the mounting unit 60 will be described. FIG. 4A shows a front view of the mounting unit 60, FIG. 4B shows a sectional view along A-A in FIG. 4A, and FIG. 4C shows a bottom view of a base member 61.

The mounting unit 60 is for fixing the above units and members, and is constituted by a lower-part base 61, a plurality of columnar members 62, a top member 63, and a plurality of leg parts 64.

The lower-part base 61, being a planar rectangular tabular member located at the lower end part of the mounting unit 60, fixes the atomization tank 11, and also fixes the lower end parts of the plurality of columnar members 62. In the present embodying mode, on four sides of the lower-part base 61, raised parts 61a projecting upward are provided, and to each raised part 61a, the lower end parts of a plurality of columnar members 62 are fixed by screw-fastening, not illustrated. In addition, at four corners of the lower-part base 61, connection ports 61b to connect the leg parts 64 for installing the spraying apparatus 1 on a floor is provided. An internal thread is formed in the connection ports 61b, and an external thread part formed in the leg portion 64 is rotatably connected thereto.

The columnar members 62 being a plurality of columnar members arranged substantially perpendicularly, are members for defining the region on the inner side of the region defined by plurality of columnar members as a region where each unit is arranged, and also for fixing each unit. As illustrated in FIG. 4B, in the present embodying mode, six columnar members 62 are utilized to define the interior region where each unit is arranged. Each columnar member 62 has the lower end part fixed to the raised part 61a of the lower-part base 61, and the upper end part is fixed to the top member 63 by screw-fastening, not illustrated. In other words, the six columnar members 62 connect the lower-part base 61 and the top member 63. In FIGS. 4A and 4B, for better understanding, the thicknesses of the raised part 61a and the columnar member 62 are enlarged.

In the middle part of the columnar members 62, a fixing part, not illustrated, for fixing the tank unit 20, the control unit 50, and the like is disposed.

In particular, above the columnar member 62, a plurality of insertion holes, not illustrated, through which bolts serving as one of functions of the fixing parts for fixing the tank unit 20 can be inserted are disposed at the same height, and by screwing the bolts into internal threads provided at a predetermined height of the unit 20, the tank unit 20 can be fixed to the columnar member 62.

In this way, by arranging each instrument in the region surrounded by the plurality of perpendicularly arranged columnar members 62, each instrument is arranged so as to be vertically stacked. Since the columnar member 62 is a member disposed outmost when viewed in plan, it is possible to dispose the later-described cover member 80 to wrap around the columnar member 62. In this situation, since the cover member 80 has a form without unevenness, the spraying apparatus 1 attached to the cover member 80 can obtain a neat appearance suitable for various environments.

Next, the top member 63 will be described with reference to FIG. 5A-5E. FIG. 5A shows a plan view of the top member 63 in a state with the top member cover 63g removed, FIG. 5B a sectional view along the A-A in FIG. 5A, FIG. 5C a bottom view of the top member 63, FIG. 5D a plan view of the top member cover 63g, and FIG. 5E a perspective view of the top member 63 and the spouting unit 30 in replenishing of the liquid formulation.

Figure 5B:
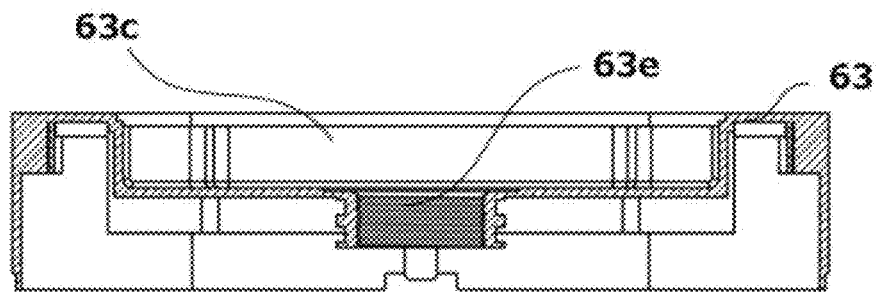

The top member 63, being a member positioned at the top of the mounting unit 60, is a member that is fixed to the upper end part of each columnar member 62, and also fixes the spouting unit 30 at the top of the entire spraying apparatus 1. As illustrated in FIGS. 5B and 5E, the top member 63 is composed of a tubular member having side walls, and having a bottomless, substantially rectangular planar shape with rounded corners.

Figure 5C:
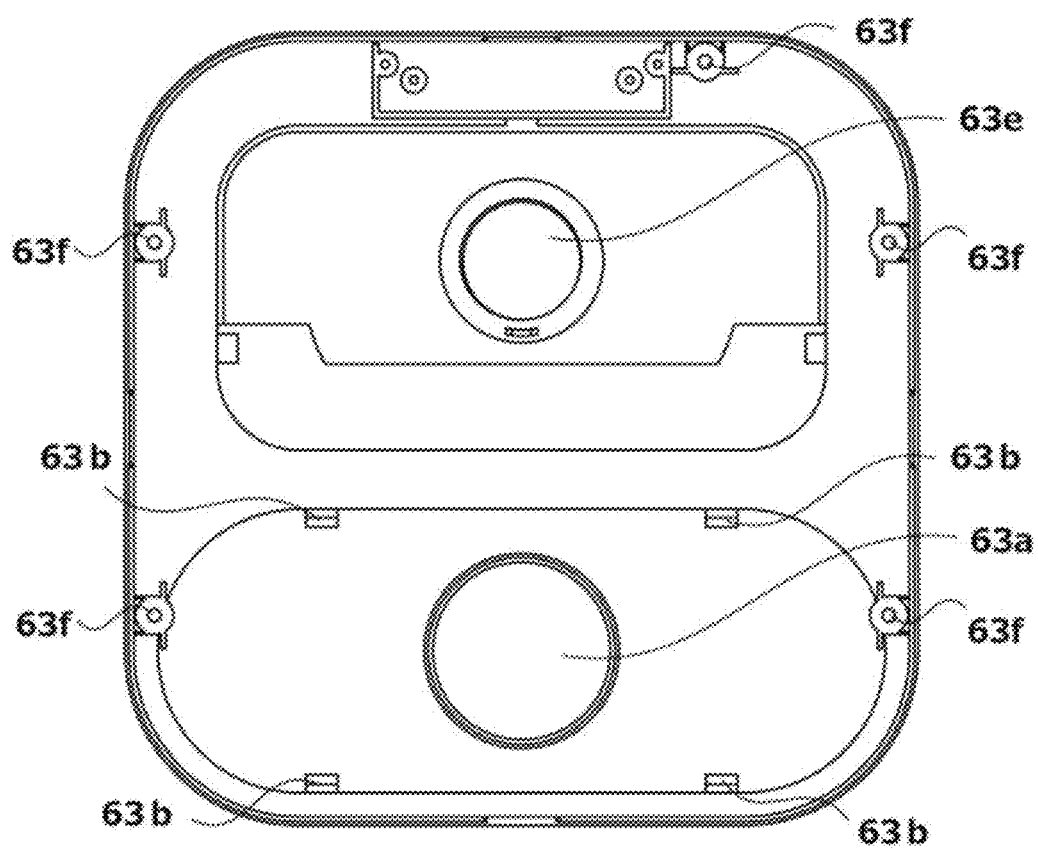
Figure 5D:
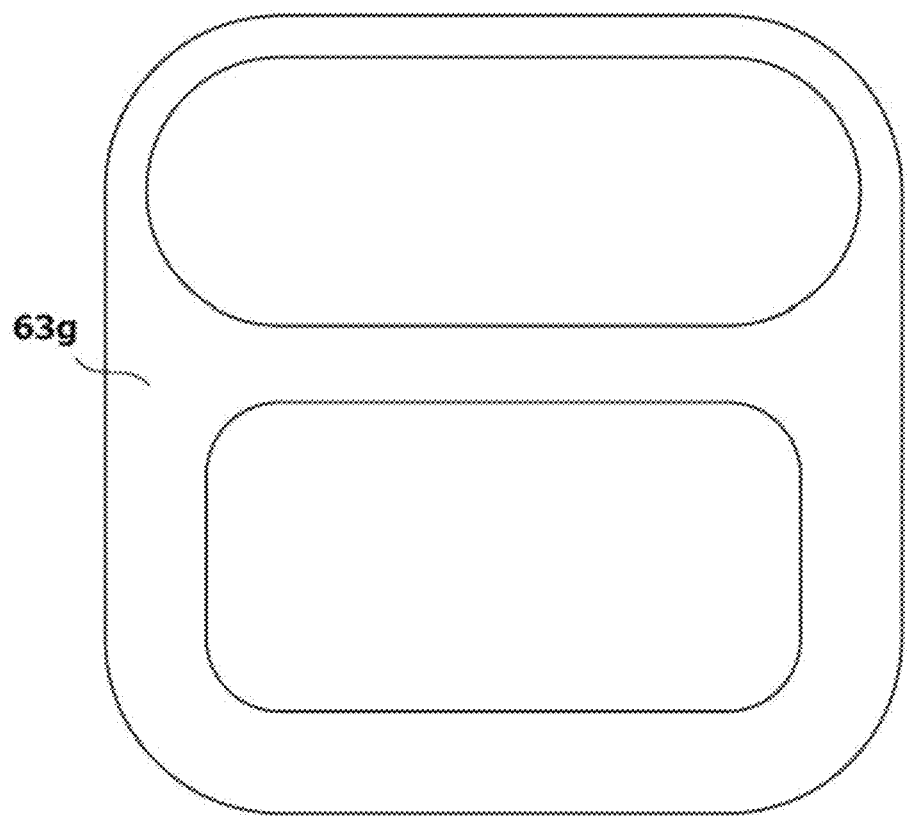
Figure 5E:
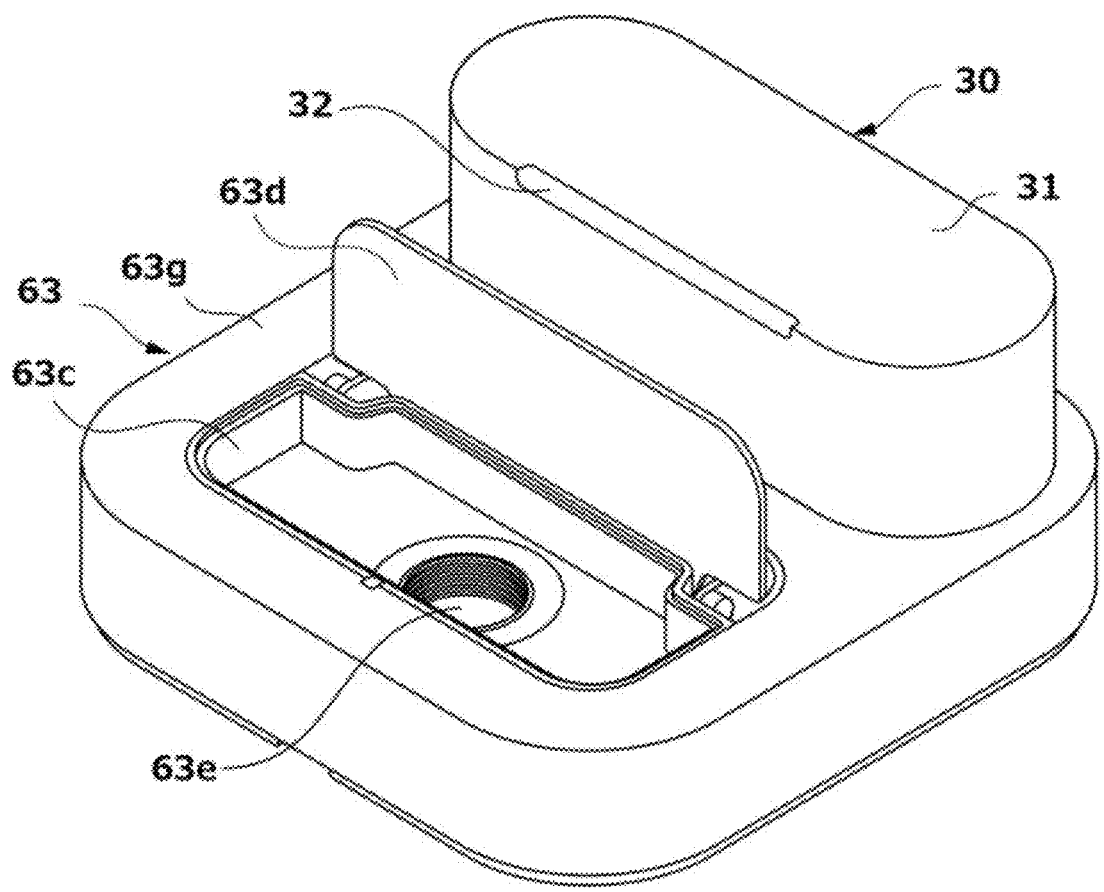

As illustrated in FIGS. 5A and 5C, open in the top panel of the top member 63 is a connection port 63a that is connected to the supply pipe 43 of the supply unit 40. At the same time, in the top panel of the top member 63, formed is a locking recess 63b to which the locking hook, not illustrated, form on the lower end part of the spouting element 31 is locked.

Furthermore, in the top panel of the top member 63, the top panel recess 63c the height of which is locally lowered downward, and the door-lid 63d that can be opened and closed that covers the top panel recess 63c are provided, and in the top panel recess 63c, the liquid-formulation replenishing port 63e connected to the inflow port, not illustrated, form in the upper surface of the tank unit 20 is provided. Formed in the inner face of the liquid-formulation replenishing port 63e is an internal thread, with which a cap member, not illustrated, having an external thread part is configured to screw and engage.

Connection between the top member 63 and the plurality of columnar members 62 is carried out by inserting bolts, not illustrated, through a plurality of screw holes 63f provided in the top panel, and screwing this bolt to internal threads, not illustrated, provided on the upper end of each columnar member 62. Alternatively, instead of providing the columnar member 62 with an internal thread, a bolt and nut may be used for connection. After connecting the top member 63 and the columnar member 62, as illustrated in FIG. 5E, the top panel of the top member 63 is covered with the top member cover 63g illustrated in FIG. 5D.

Configuration of Power Supply Unit 70

The power supply unit 70 is a unit that is connected to a household or commercial power supply to supply power to each instrument. Specifically, the power supply unit 70 includes a cable connected to a power tap, a power switch 71 of the spraying apparatus 1 itself, and the like.

Configuration of Cover Member 80

The cover member 80 is a member that is arranged on the periphery of the plurality of columnar members 62 and covers each instrument.

Specifically, as illustrated in FIG. 1A, it is arranged wound on the periphery of the plurality of columnar members 62 so as to cover the height from below the top member 63 to the lower-part base 61. The cover member 80 is formed by inflecting an elastic stainless steel tabular member by bending.

Here, in configuring the spraying apparatus 1, since each instrument such as the atomizing unit 10 and the tank unit 20 is arranged in the region surrounded by the plurality of perpendicularly arranged columnar members 62, the columnar member 62 is disposed outermost when viewed in plan. Therefore, the cover member 80 can be arranged so as to be wound around the columnar members 62. In this situation, since the cover member 80 has a form without unevenness, the spraying apparatus 1 attached to the cover member 80 can obtain a neat appearance suitable for various environments.

Spraying Method Employing Spraying Apparatus 1

Next, with reference to a flowchart shown in FIG. 6, a method of atomizing liquid formulation employing a spraying apparatus 1 according to the present embodying mode will be described.

Step S100: Replenish Liquid Formulation

First, prior to starting of the spraying apparatus 1, a liquid formulation is replenished to the tank unit 20 (Step S100).

When replenishing the tank unit 20 with the liquid formulation, a user opens a door-lid 63d that can be opened and closed provided in the top panel of the top member 63, removes a cap, not illustrated, attached to the liquid-formulation replenishing port 63e, and pours the liquid formulation into the liquid-formulation replenishing port 63e formed in the top panel recess 63c. After replenishing with the liquid formulation, the cap is tightened and the door-lid 63d is closed.

In this way, since the liquid-formulation replenishing port 63e is covered with the door-lid 63d that can be opened and closed, the liquid-formulation replenishing port 63e can be covered with the door-lid 63d when not in use, so that appearance can be maintained. In particular, since the liquid-formulation replenishing port 63e is formed in the top panel recess 63c, when the door-lid 63d is closed, the top panel of the top member 63 has the same plane except for the spouting unit 30, thereby exhibiting a particularly excellent appearance.

Step S110: Start Suppling Liquid Formulation

In Step S100, when the tank unit 20 is replenished with the liquid formulation, the user connects a power cord, not illustrated, that constitutes the power supply unit 70 to a general household or commercial power supply, and then turns on a power supply switch 71 that likewise that constitutes the power supply unit 70. When the power switch 71 is turned on, the control unit 50 operates the liquid supply pump 41 to start supplying the liquid formulation supplied to the tank unit 20 to the atomization tank 11 (Step S110).

The liquid formulation stored in the tank unit 20 is supplied to the atomization tank 11 as follows. That is, the liquid formulation supply pump 41 is driven by a signal from the control unit 50, and accordingly the liquid formulation flows out through a connection port, not illustrated, formed in the bottom surface of the tank unit 20, passes through the liquid formulation supply tube 42 and the liquid formulation supply pump 41, and flows into the atomization tank 11 interior through the supply port 11a formed in the upper surface of the atomization tank 11.

Steps S120-S130: Determine Second Liquid Level-Halt Liquid Formulation Supply

At the same time as the supply of the liquid formulation begins in Step S110, the control unit 50 begins determination of the liquid level by the liquid-level sensor 15, determining whether the liquid level in the atomization tank 11 has reached a predetermined second liquid level h2 (Step S120).

If the liquid level detected by the liquid-level sensor 15 does not reach the second liquid level h2, that is, "N" in Step S120, the control unit 50 continues the supply by the liquid-formulation supply pump 41, whereas if the second liquid level h2 is reached, that is "Y" in Step S120, the control unit 50 halts the supply by the liquid-formulation supply pump 41 (Step S130).

Step S140: Atomization of Liquid Formulation

In Step S130, if the supply of the liquid formulation is halted, the control unit 50 begins the atomization of the liquid formulation in the atomizing unit 10 (Step S140). Beginning the atomization un in Step S140 may be controlled to be triggered by the liquid level detected by the liquid-level sensor 15 reaching the first liquid level h1. In that case, the atomization operation and the supply of the liquid formulation are performed at the same time, which is preferable because the atomization operation can be started early.

When atomization of the liquid formulation is carried out in the atomizing unit 10, the control unit 50 begins blowing of the conveyance air by the blower 13, and at the same time, begin the atomization of the liquid formulation by the atomizing device 12.

Figure 2A:
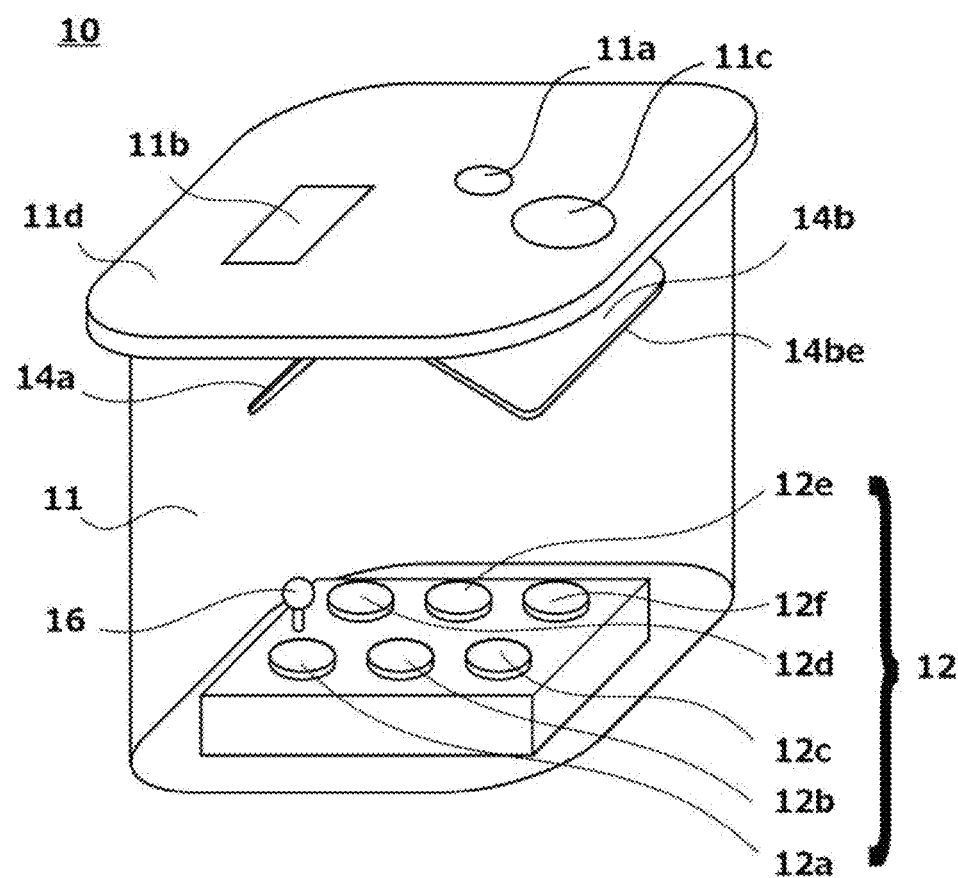
Figure 2B:
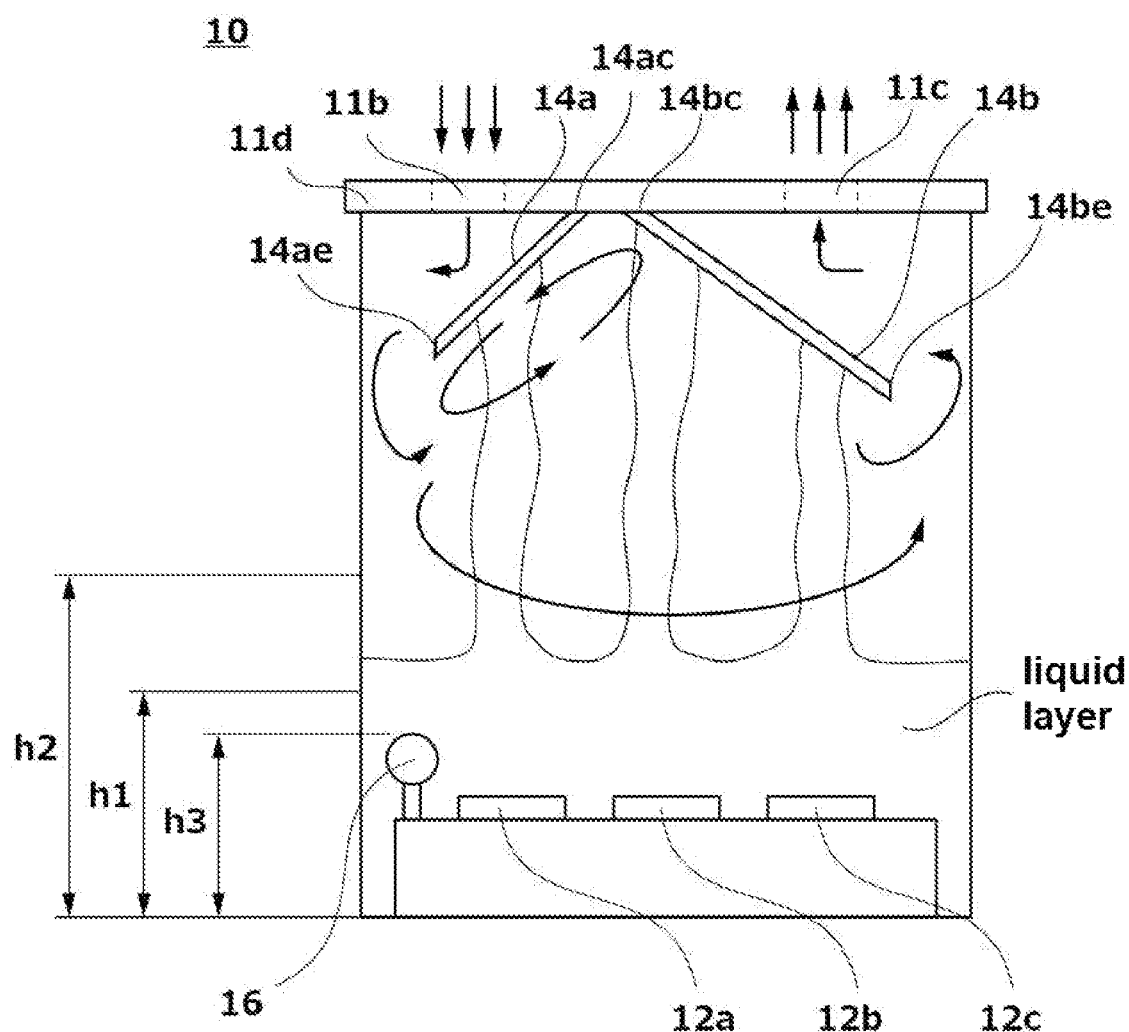

Along with the operation of the atomizing device 12, as illustrated in FIG. 2B, the liquid column rises above each of the ultrasonic vibrators 12a, 12b, 12c . . . . While the liquid column contains particles of various particle sizes, the liquid droplets of large particle diameter contained in the liquid column contact the baffle plates 14a and 14b arranged inclined diagonally downward above the ultrasonic vibrator for contact with the liquid column, flow downward, and flow back to the stored liquid layer, whereas only the mist droplets of small particle diameter float in the air.

In addition, along with the operation of the blower 13, the conveyance air is supplied downward from the blow port 11b, conveying and sending out the mist droplets of small particle diameter floating in the air from the send-out port 11c.

At this time, since the baffle plate 14a provided along one widthwise end of the atomization tank 11 is arranged underneath the blow port 11b and above the ultrasonic vibrators 12a and 12d along one widthwise end, the conveyance air supplied through the blower 13 is prevented from directly reaching the liquid surface and the liquid column, and also the liquid column and the liquid droplets rising from the liquid surface is prevented from flowing from the blow port 11b and directly reaching the blower 13. Therefore, atomization of the liquid formulation and supply of the conveyance air function without interfering with each other, thereby ensuring the performance of particle size sorting.

In addition, the conveyance air supplied through the blower 13 collides against one side of the surface of the baffle plate 14a, and flows along one side of the surface of the baffle plate 14a, and then pressure loss occurs, resulting in drop in pressure for conveying particles. Because the pressure of the conveyance air drops, from the liquid formulation that has been separated into liquid droplets and tiny particles by colliding against the baffle plates 14a and 14b, only fine particles still smaller than particles of size at the level allowing normal conveyance are conveyed by the conveyance air.

In addition, when the conveyance air that has flowed along one side of the surface of the baffle plate 14a flows out between the edge piece 14ae and the surface along one end of the atomization tank 11, a negative pressure region forms along the baffle plate 14a on the other side of the surface, that is, the region that the liquid column comes into contact with. In the negative pressure region, the pressure of the conveyance air drops still further, and therefore particles other than fine particles that are of extraordinarily tiny particle diameter cannot be conveyed, meaning they fall to the liquid surface below. Consequently, fine particles of particle diameter tiny to a level that can give rise to Brownian motion can alone be conveyed downstream by the conveyance air.

A mechanism like this affords a spraying apparatus that, more than simply receiving liquid columns at the baffle plate makes possible conveying minute particles by means of conveyance air, and enables the selective spraying of only fine particles that are tiny to a level that can give rise to Brownian motion.

In addition, the baffle plate 14a is arranged inclined diagonally downward, with one end having the connection part 14ac (first connection [piece] portion) connected to the top panel 11d of the atomization tank 11, and the other end having the edge part 14ae (first edge portion) spaced apart at a predetermined spacing from the lateral surface along one widthwise end of the atomization tank 11. In order to allow the conveyance air supplied through the blower 13 to pass through the outer peripheral side in the atomization tank 11, it is arranged protruding from the inside toward the outside.

Owing to this sort of structure of the baffle plate 14a, the conveyance air supplied downward through the blow port 11b changes its flow direction diagonally downward according to the orientation in which baffle plate 14a is arranged, and having passed through the gap formed between the lateral surface along one widthwise end of the atomization tank 11 and the edge piece 14ae of the baffle plate 14a, arrives at the bottom portion of the atomization tank 11 near the liquid layer. The conveyance air that has reached the bottom switches the direction toward the lateral surface along the other widthwise end, and circulates in the vicinity of the liquid surface toward the lateral surface along the other widthwise end of the atomization tank 11. Then, it switches the direction upward in the vicinity of the lateral surface along the other widthwise end of the atomization tank 11, and flows toward the send-out port 11c formed in the top panel 11d. In addition, having passed through the gap formed between the lateral surface along one widthwise end of the atomization tank 11 and the other end part of the baffle plate 14a, part of the conveyance air winds in on the surface along the liquid-column receiving side of the baffle plate 14a, and then forms a swirling flow in the atomization tank 11 and flows out through the send-out port 11c.

In this way, the conveyance air supplied downward through the blow port 11b forms a gently swirling flow in the interior part of the atomization tank 11 according to the orientation in which baffle plate 14a is arranged, part of it winds in on the surface along the liquid-column receiving side, and then part of it, having passed through the outer peripheral side in the atomization tank 11 is sent out through the send-out port [11b] 11c.

Since the conveyance air supplied through the blow port 11b passes through the outer peripheral side in the atomization tank 11 and forms a gently swirling flow, owing to the centrifugal-force effect that accompanies the production of the swirling flow, the minute particles are further separated from even more minute fine particles, and the fine particles alone are conveyed on the conveyance air.

Furthermore, in the present embodying mode, the blow port 11b and the send-out port 11c are provided on the top panel 11d of the atomization tank 11 and in locations on opposite sides from each other, with the baffle plate 14a being put in between.

Therefore, the swirling flow in which the baffle plate 14a is interposed can be formed, and thus the effect of centrifugal separation by the swirling flow can be heightened.

The atomizing unit 10 in the present embodying mode designed in this way enables, by collaboration between the blower 13 and the baffle plate 14a, selectively generating and sending out only fine particles that are tiny to a level that can give rise to Brownian motion.

In addition, in the present embodying mode, the baffle plate 14b is arranged inclined diagonally downward, toward the opposite side from the baffle plate 14a, in such a manner that one end has a connection part 14bc (second connection portion) connected to the top panel of the atomization tank 11, and the other end has an edge part 14be (second edge portion) arranged spaced apart at a predetermined spacing from the lateral surface along the other widthwise end of the atomization tank 11, that is, on the side opposite from the side where the baffle plate 14a is arranged.

The baffle plate 14b is arranged underneath the send-out port 11c and above the ultrasonic vibrators 12c and 12f along the other widthwise end. Therefore, the liquid droplets of large particle diameter contained in the liquid column produced by the ultrasonic vibrators 12c and 12f come into contact with the lower surface of the baffle plate 14b, flow downward, and flow back to the stored liquid layer, whereas only the mist droplets of small particle diameter float in the air.

At this time, because the pressure of the conveyance air has dropped due to contact with the baffle plate 14a, only fine particles still smaller than particles of size at the level allowing normal conveyance are conveyed by the conveyance air. In this way, also among particles produced in the vicinity of the baffle plate 14b, only fine particles of tiny diameter can be selectively conveyed.

In addition, the blow port 11*b* is provided to one widthwise end of the connection part 14*ac* of the baffle plate 14*a* in the top panel 11*d* of the atomization tank 11, and meanwhile the send-out port 11*c* is provided to the other widthwise end of the connection part 14*bc* of the baffle plate 14*b*, by which the swirling flow formed in the atomization tank 11 interior becomes so large that is formed throughout the entire atomization tank 11 with the baffle plate 14*a* and baffle plate 14*b* interposed. Therefore, the selection of fine particles by the centrifugal force of the conveyance air is further enhanced, fine particles that are minute to a level that can give rise to Brownian motion alone can be reliably selected and sprayed.

Steps S150-S160: Determine First Liquid Level-Begin Replenishment of Liquid Formulation Reference is made back to the flowchart in FIG. 6. In Step S140, when the atomization of the liquid formulation begins, the control unit 50 begins to determine the liquid level by the liquid-level sensor 15, determining whether the liquid level in the atomization tank 11 has fallen below the first liquid level h1 (Step S150).

If the liquid level detected by the liquid-level sensor 15 has secured the first liquid level h1, that is, "N" in Step S150, the control unit 50 continues the atomization intact, and if it falls below the first liquid level h1, that is "Y" in Step S150, the control unit 50 begins replenishment of the liquid formulation by the liquid-formulation supply pump 41 (Step S160).

The replenishment of the liquid formulation in Step S160 is carried out by operating of the liquid-formulation supply pump 41, as in Step S110. In this case, the atomization tank 11 can be replenished with the liquid formulation by the liquid-formulation supply pump 41 at the same time while the atomization operation is continued.

In particular, since the supply port 11*a* is formed above the baffle plate [11*b*] 14*b*, the liquid formulation supplied through the supply port 11*a* passes along the baffle plate [11*b*] 14*b*, and in a liquid state, fall to the liquid layer stored in the atomization tank 11 interior. That is, the liquid formulation supplied through the supply port 11*a* is replenished in the liquid layer without being affected by the ultrasonic vibration. Therefore, the liquid formulation can be replenished without affecting the fine-particle selection performance in the present embodying mode.

Steps S170-S180: Determine Second Liquid Level-Halt the Liquid Formulation Supply At the same time as the replenish of the liquid formulation begins in Step S160, the control unit 50 begins determination of the liquid level by the liquid-level sensor 15, determining whether the liquid level in the atomization tank 11 has reached a second liquid level h2 higher than the predetermined first liquid level h1 (Step S170).

If the liquid level detected by the liquid-level sensor 15 does not reach the second liquid level h2, that is, "N" in Step S170, the control unit 50 continues the supply by the liquid-formulation supply pump 41, whereas if the second liquid level h2 is reached, that is "Y" in Step S170, the control unit 50 halts the supply by the liquid-formulation supply pump 41 (Step S180).

Thereafter, until the user turns off the power switch 71, the processing may be controlled to return to Step S150 and repeat the processes from determination of the first liquid level to supply of the liquid formulation.

By doing so, the liquid level of the liquid formulation in the atomization tank 11 can be maintained between the first liquid level h1 and the second liquid level h2, allowing the user to automatically continue the operation over a long time without paying attention to the increase or decrease in the liquid level.

In addition, the control unit 50 may be configured so as to always determine, by utilizing the halt sensor 16, whether or not the liquid level has fallen below a third liquid level h3 lower than the first liquid level h1. If the halt sensor 16 detects that the liquid level has fallen below the third liquid level h3, the control unit 50 immediately halts the operation of the blower 13 and the atomizing device 12.

By doing so, it is possible to keep the atomizing device 12 from operating in situations where the liquid formulation is extremely scant, thereby preventing so-called empty-tank running.

In addition, at this time, the control unit 50 may be configured to notify, at the same time as halting the operation, the user of a state in which the apparatus is run on an empty tank by means of sounding an alarm sound or turning on a warning light. With this configuration, the user can realize an empty-tank running state.

Adjustment of Particle Diameter Employing Spraying Apparatus 1

Next, a method of adjusting the particle diameter of fine particles to be sprayed by employing the spraying apparatus 1 of the present embodying mode to a desired value will be described.

As described above, the control unit 50 can control the rpm of the blowing element of the blower 13 by controlling the voltage applied to the blower 13. Then, by raising the rpm of the blowing element, the particle diameter of the fine particles sprayed from the spray port 32 can be made smaller. Conversely, by lowering the rpm of the blowing element, the fine particles sprayed from the spray port can be made larger. The mechanism by which the particle diameter of the sprayed particles can be changed in accordance with the change in the rpm of the blowing element will be described below.

In general, when the rpm of the blowing element is controlled, the fanning volume changes as the rpm changes. For example, by raising the rpm of the blowing element, the fanning volume is increased, and by lowering the rpm, the fanning volume is decreased. However, since the air pressure itself does not change, the conveying capacity of the conveyance air does not change, and it is not possible to change the particle diameter of conveyable particles by changing the rpm.

On the other hand, in the present invention, since the blow port 11*b* for the conveyance air supplied from the blower 13 is arranged above the baffle plate 14*a*, the conveyance air supplied through the blow port 11*b* collides against the surface on one side of the baffle plate 14*a*, and pressure loss occurs.

By controlling the rpm of the blowing element in a state in which pressure loss in the conveyance air has been brought about, change in air pressure with respect to change in conveyance-air fanning volume can be made larger. For example, by raising the rpm of the blowing element, the fanning volume of the conveyance air is increased, thereby pressure loss produced by contact with the baffle plate 14*a* is increased, and therefore pressure of the conveyance air drops, and capacity for conveying particles is made smaller. Therefore, compared to before changing of the rpm, particles of tiny particle size are conveyed.

Conversely, by lowering the rpm of the blowing element, the fanning volume of the conveyance air is decreased, thereby pressure loss caused produced by contact with the baffle plate 14*a* is decreased, and therefore pressure of the conveyance air rises, and capacity for conveying particles is improved. Therefore, compared to before changing the rpm, particles whose diameter is large are conveyed In this way, by exploiting the increase or decrease in pressure loss, it is possible to change the particle diameter of the conveyable particles.

In addition, in the present embodying mode, the conveyance air, after having gone through the spacing formed between the edge piece 14ae of the baffle plate 14a and the atomization tank 11, winds in on the surface along the liquid-column receiving side in the baffle plate 14a and then arrives at the send-out port 11c, surrounding the baffle plate 14a gently swirling flow of the conveyance air directed to the send-out port.

By controlling the rpm of the blowing element, the fanning volume is changed, and therefore centrifugal force applied to the atomized particles is changed, that is, the particle diameter of conveyable particles can be changed. For example, by raising the rpm of the blowing element, the fanning volume of the conveyance air is increased, thereby the centrifugal force applied to the particles accompanying the swirling flow is increased, particles of relatively tiny particle diameter are separated, and therefore only particles of extraordinarily tiny particle diameter are conveyed.

Conversely, by lowering the rpm of the blowing element, the fanning volume of the conveyance air is reduced, thereby the centrifugal force applied to the particles accompanying the swirling flow is decreased, capacity for separating the particles is weakened, and particles whose diameter is large are made conveyable.

In this way, by controlling the rpm of the blowing element of the blower 13 by the control unit 50, it is made possible to spray fine particles of a desired particle size from the spray port 32.

Modification 1

Figure 6:
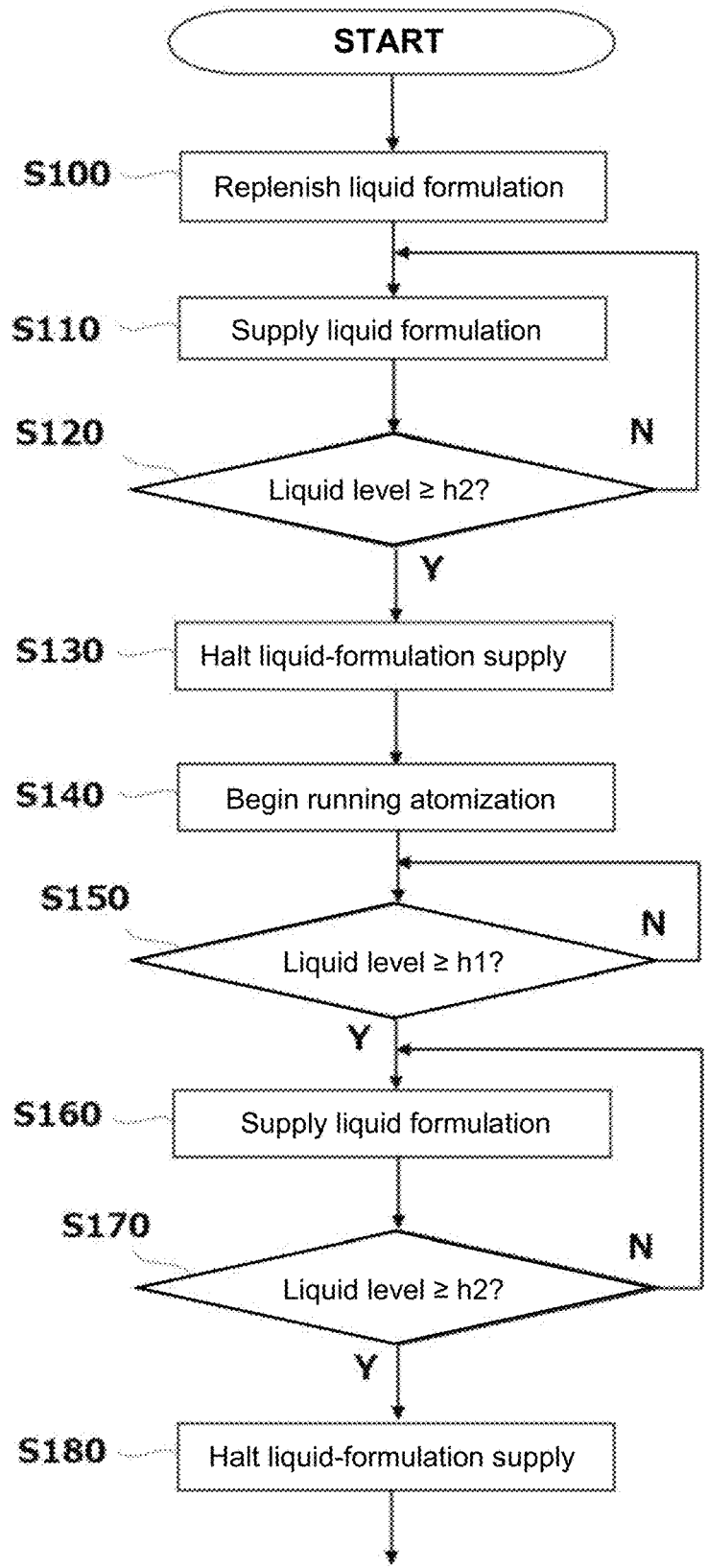

In Step S110 of the flowchart shown in FIG. 6, the liquid formulation is supplied to the atomization tank 11 from the tank unit 20 by utilizing the liquid-formulation supply pump 41, but a configuration in which in place of the liquid-formulation supply pump 41, a solenoid valve is employed to supply the liquid formulation.

In other words, in the midway through the liquid-formulation supply tube 42, a solenoid valve that can be opened and closed in response to a signal from the control unit 50 is arranged, such that when the control unit 50 issues an open signal, the solenoid valve is released to supply the liquid formulation. At this time, since the tank unit 20 is arranged beneath the atomization tank 11, the liquid formulation can be supplied exploiting gravity, and the liquid formulation can be supplied more rapidly and with less power consumption than by employing the liquid-formulation supply pump 41. In particular, when the liquid formulation is supplied to the atomization tank 11 at the time of start-up, by supply exploiting gravity, the time from turning on the power switch 71 until beginning atomization can be shortened, and an easy-to-use spraying apparatus 1 can be afforded.

Modification 2

With reference to FIG. 7A-7D, modification of the configuration of the atomizing unit 10 will be described. Instead of arranging inclined diagonally downward, the baffle plates 14a and 14b can be arranged perpendicularly downward from the top panel and then arranged inflecting horizontally toward the lateral surface of the atomization tank 11.

Figure 7A:
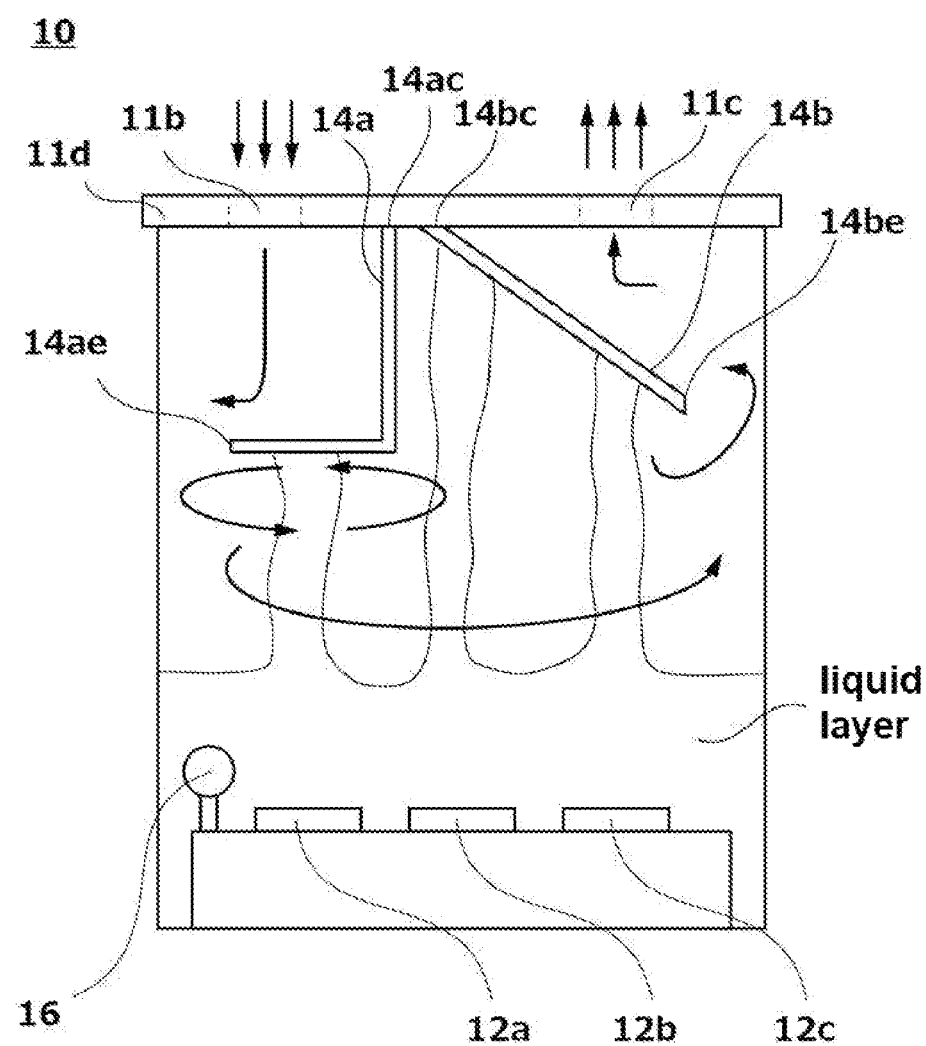

In particular, as illustrated in FIG. 7A, the baffle plate 14a is drooped perpendicularly downward from the top panel 11d and then inflected horizontally toward the lateral surface along one widthwise end of the atomization tank 11, with the edge piece 14ae disposed spaced apart at a predetermined spacing from the lateral surface along one widthwise end of the atomization tank 11. With this configuration, in the same manner as described above, the conveyance air from the blower 13 can be brought into contact with the surface on one side of the baffle plate 14a to cause pressure loss. As a result, a spraying apparatus 1 can be made available that is capable of conveying only fine particles from the liquid column that has come into contact with the other side of the surface of the baffle plate 14a, and selectively spraying only fine particles that are tiny to a level that can give rise to Brownian motion.

In addition, also with such configuration of the baffle plate 14a, the conveyance air can pass between the edge piece 14ae and the lateral surface along one widthwise end of the atomization tank 11, and pass underneath the baffle plate 14a, and thereby forming a swirling flow in the atomization tank 11 interior. As a result, a spraying apparatus 1 can be made available that is capable of, by exploiting effect of centrifugal separation, conveying only fine particles from the liquid column that has come into contact with the other side of the surface of the baffle plate 14a, and selectively spraying only fine particles that are tiny to a level that can give rise to Brownian motion.

Modification 3

The blow port 11b and the send-out port 11c can be arranged, not in the top panel 11d of the atomization tank 11, but in the lateral surface.

Figure 7B:
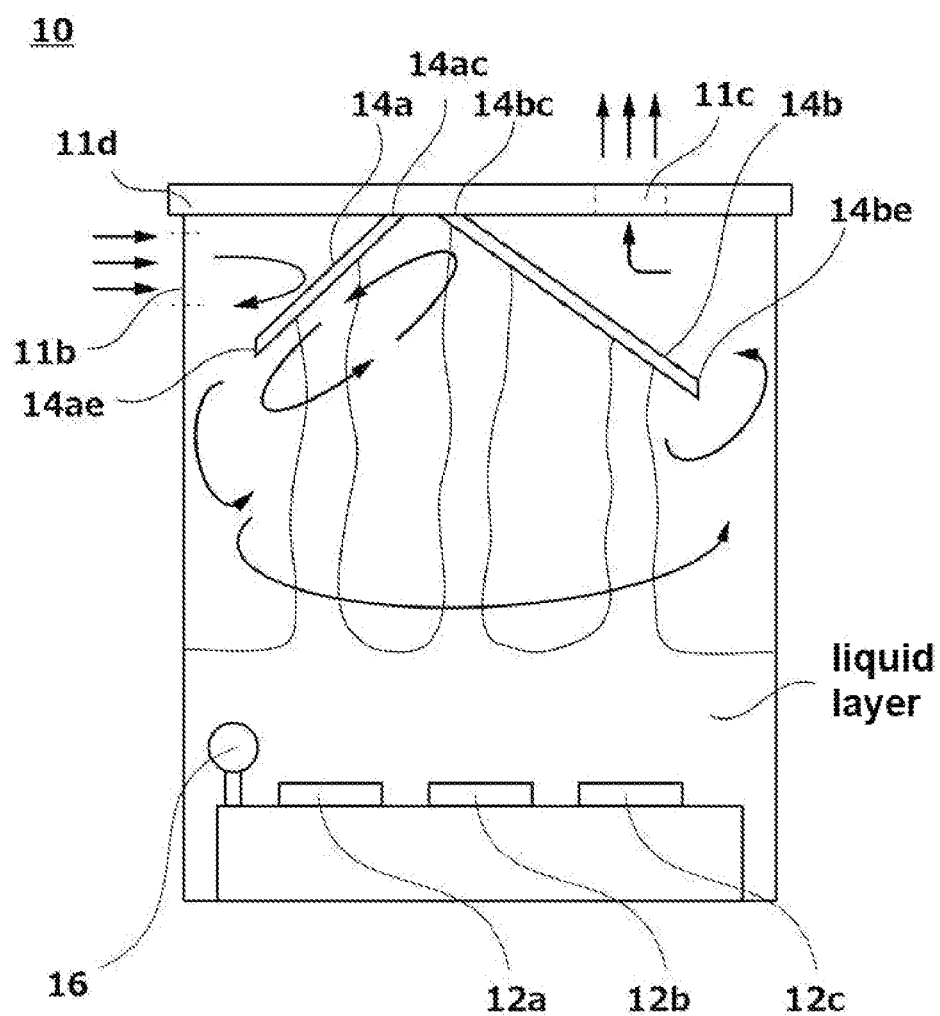

As illustrated in FIG. 7B, even in instances in which the blow port 11b is arranged in the lateral surface along one widthwise end of the atomization tank 11, as long as it is arranged above the position of the edge piece 14ae, because the conveyance air that has flowed in through the blow port 11b comes into contact with the baffle plate 14a, the pressure loss of the conveyance air is occurred, and the same effect as described above can be obtained.

Figure 7C:
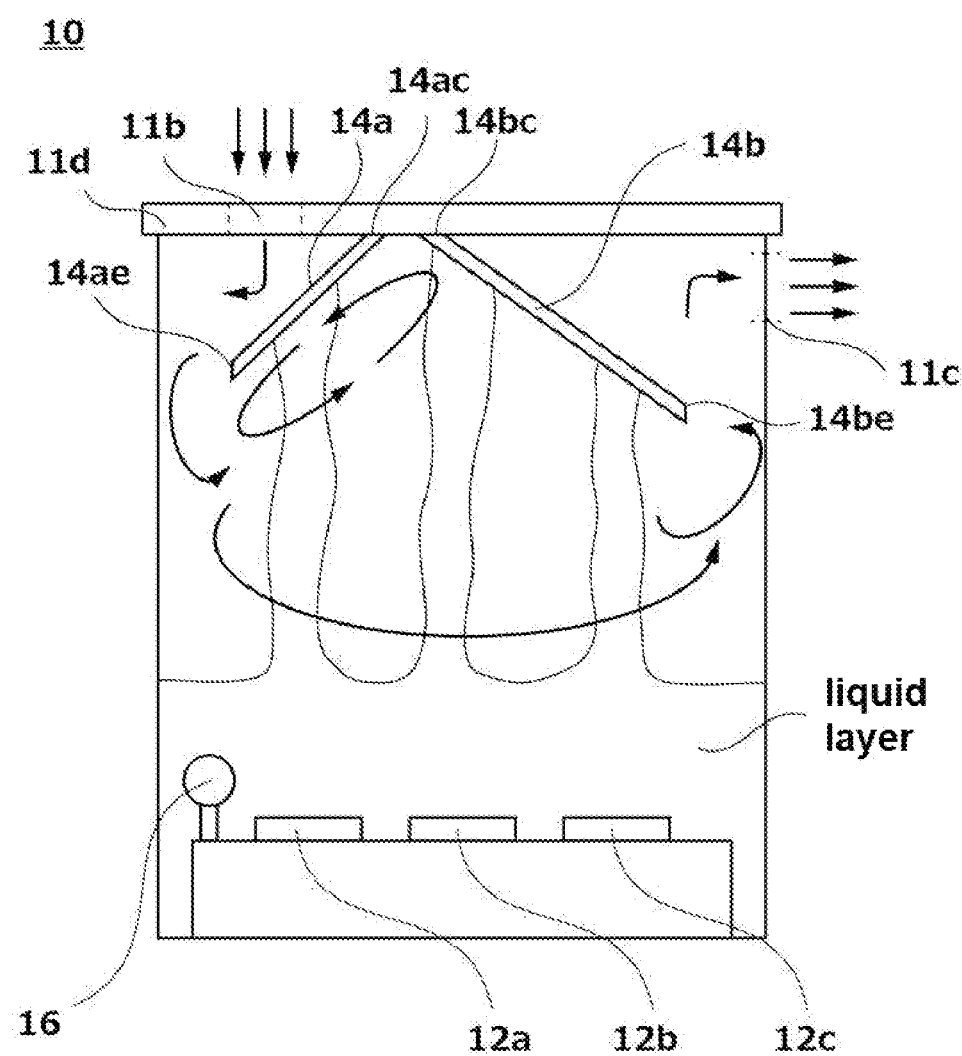

In addition, as illustrated in FIG. 7C, even in instances in which the send-out port 11c is arranged in the lateral surface along the other widthwise end of the atomization tank 11, as long as it is arranged above the position of the edge piece 14be, a swirling flow can be formed in the atomization tank 11 interior, and the same effect as described above can be obtained.

Figure 7D:
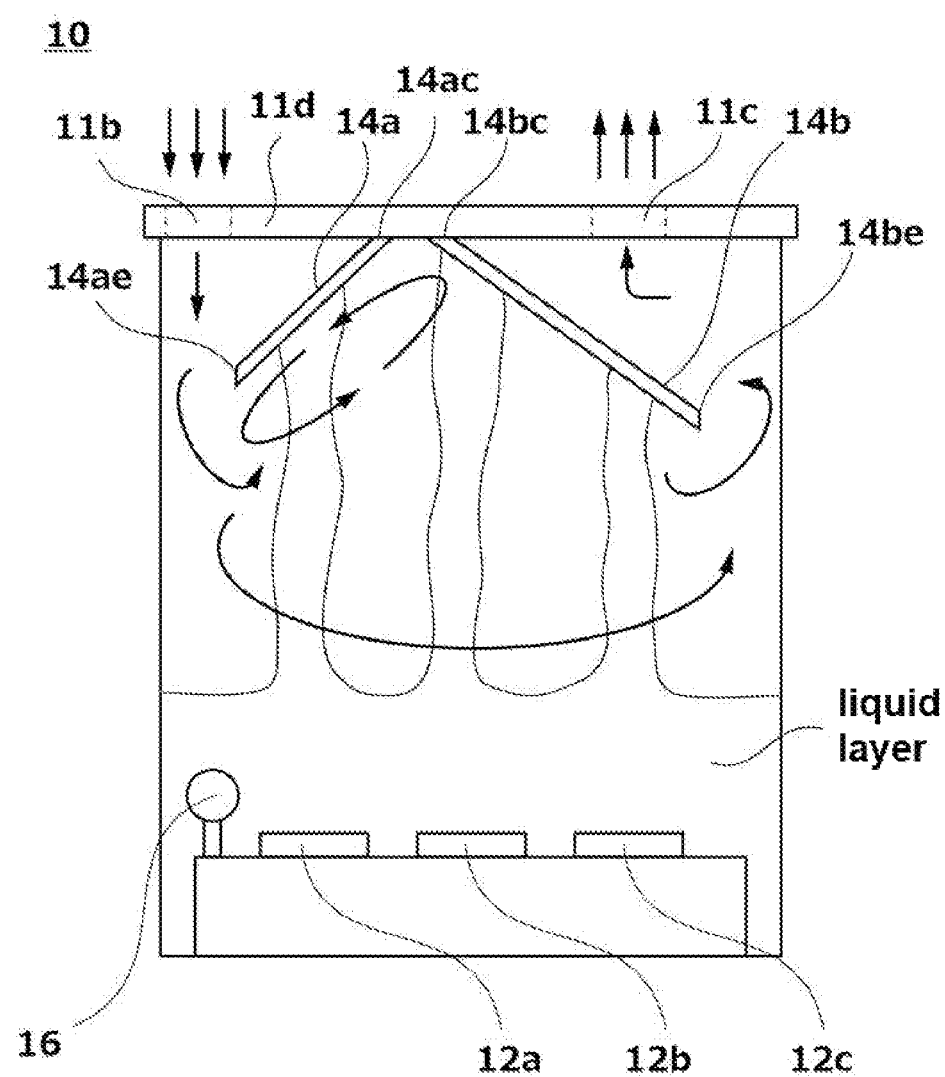

In addition, as illustrated in FIG. 7D, the position where the blow port 11b is arranged may be arranged in a position with which the conveyance air that has flowed in does not come into contact with the baffle plate 14a. Even in such instances, because the conveyance air passes between the lateral surface along one widthwise end of the atomization tank 11 and the edge piece 14ae and passes underneath the baffle plate 14a, swirling flow can be formed in the atomization tank 11 interior, and the same effect as described above can be obtained.

In this way, baffle plates 14a and 14b the arrangement or form of which has been changed, or blow port 11b and the send-out port 11c the arrangement of which has been changed, still fall within the scope of the present invention, as long as the phenomenon described with respect to the present invention can be occurred.

The effects of the present invention described above can be summarized as follows.

Because the baffle plate 14a arranged to receive the liquid column of the liquid formulation produced by, among the ultrasonic vibrators, the ultrasonic vibrators 12a and 12d arranged along one widthwise end, and the baffle plate 14b arranged to receive the liquid column of the liquid formulation produced by the ultrasonic vibrators 12c and 12f arranged along the other widthwise end are provided, the liquid column comes into contact with the baffle plates 14*a* and 14*b* arranged above each of the ultrasonic vibrators 12*a*, 12*b*, 12*c* . . . , liquid droplets of large particle diameter contained in the liquid column comes into contact with the baffle plates 14*a* and 14*b*, flow downward, and flow back to the stored liquid layer, and meanwhile, only large amount of mist droplets of small particle diameter float in the air and are conveyed on the conveyance air.

At this time, the baffle plate 14*a* is furnished with the edge part 14*ae* disposed spaced apart at a predetermined spacing from the inner face along one widthwise end in the atomization tank 11, and the connection part 14*ac* connected to the inner side of the atomization tank 11, wherein the blow port 11*b* is arranged more toward one widthwise end of the atomization tank 11 than the connection part 14*ac* is, and the baffle plate 14*b* is furnished with the edge part 14*be* disposed spaced apart at a predetermined spacing from the inner face along the other widthwise end in the atomization tank 11, and the connection part 14*bc* connected to the inner side of the atomization tank 11, wherein the send-out port 11*c* arranged more toward the other widthwise end of the atomization tank 11 than the connection part 14*bc* is, and thereby, in the atomization tank 11 interior, a large swirling flow is formed over the entire atomization tank 11 with the baffle plate 14*a* and baffle plate 14*b* interposed. Therefore, owing to the centrifugal-force effect that accompanies the production of the swirling flow, minute particles and even more minute fine particles are separated, and a spraying apparatus 1 can be made available that is capable of reliably selecting and spraying a large volume of fine particles that are minute to a level that can give rise to Brownian motion alone.

In addition, since the baffle plate 14*a* is arranged so that the conveyance air supplied through the blow port 11*b* comes into contacts the surface on one side of the baffle plate 14*a*, and therefore on that occasion a pressure loss occurs, with the pressure for conveying the particles dropping. Because the pressure of the conveyance air drops, from the liquid formulation that has been separated into liquid droplets and tiny particles by colliding against the baffle plate 14, only fine particles still smaller than particles of size at the level allowing normal conveyance can be conveyed by the conveyance air.

In addition, because the send-out port 11*c* is arranged on the opposite side from the blow port 11*b* with respect to the connection part 14*ac* of the baffle plate 14*a*, the conveyance air that comes into contact with the baffle plate 14*a* goes through the spacing formed between the edge part 14*ae* of the baffle plate 14*a* and the inner face of the atomization tank 11 and arrives at the send-out port 11*c*. On that occasion, a negative pressure region forms along the baffle plate 14*a* on the reverse side of the surface that the conveyance air comes into contact with, that is, the region that the liquid column comes into contact with, and because in the negative-pressure region the pressure of the conveyance air drops still further, particles other than fine particles that are of extraordinarily tiny particle diameter cannot be conveyed, meaning they fall to the liquid surface below. Consequently, fine particles of particle diameter tiny to a level that can give rise to Brownian motion can alone be conveyed toward the send-out port 11*c* by the conveyance air.

In addition, the conveyance air supplied through the blow port 11*b*, after having gone through the spacing formed between the edge piece 14*ae* of the baffle plate 14*a* and the atomization tank 11, winds in on the surface along the liquid-column receiving side, and then arrives at the send-out port 11*c*, surrounding the baffle plate 14*a* gently swirling flow of the conveyance air directed to the send-out port 11*c*. When minute particles separated from the liquid droplets by the collision of the liquid column against the baffle plate 14*a* are carried by the conveyance air, owing to the centrifugal-force effect that accompanies the production of the swirling flow, the minute particles are further separated from even more minute fine particles, and the fine particles alone are conveyed on the conveyance air. Designing in this way affords a spraying apparatus that, thanks to the effect of the baffle plate 14*a* and the effects of the swirling flow, is capable of sending out through the send-out port 11*c* solely fine particles in conjunction with conveyance air.

In addition, because the blow port 11*b* and the send-out port 11*c* are provided on the top panel 11*d* on opposite sides from each other with the baffle plate 14*a* interposed therebetween, a swirling flow in which the baffle plate 14*a* is interposed can be formed, and because the effect of centrifugal separation by the swirling flow can be heightened, a spraying apparatus 1 capable of spraying solely fine particles of tiny diameter can be made available.

In addition, because the baffle plate 14*a* is disposed above the ultrasonic vibrators 12*a* and 12*d* and below the blow port 11*b*, in an orientation blocking liquid columns produced by the ultrasonic vibrators 12*a* and 12*d*, and conveyance air supplied from the blow port 11*b*, the liquid columns produced by the movement of the ultrasonic vibrators 12*a* and 12*d* can be prevented from being blown directly into the blower 13, and meanwhile conveyance air from the blower 13 can be prevented from blowing directly onto the liquid columns. Therefore, a spraying apparatus 1 can be made available that is capable of conveying by means of conveyance air solely minute particles, without spoiling the particle-sorting effect due to the baffle plate 14*a*.

In addition, because in instances in which the liquid level in the atomization tank 11 falls below the predetermined first liquid level h1, supply of the liquid formulation stored in the tank unit 20 is controlled so as to be started, and when the predetermined second level h2 is reached the supply is halted, despite the liquid formulation in the atomization tank 11 interior being consumed as a consequence of an atomization run, the liquid level in the atomization tank 11 interior can be kept between the first liquid level h1 and the second liquid level h2. Accordingly, even in instances in which a large volume of liquid formulation is sprayed over a broad range, the spraying can be stably and automatically continued over a long period of time. And then, because scaling up of the atomization tank 11 can be held back, the capacity of the blower 13 can be made small, affording a spraying apparatus 1 enabling only fine particles of that much tinier particle diameter—that is, only fine particles tiny to a level that can give rise to Brownian motion—to be selected and conveyed.

In addition, because a halt sensor 16 that detects a third liquid level h3 lower than the first liquid level h1 is provided, and the operation of the blower 13 and the atomizing device 12 is halted when the halt sensor 16 senses a fall below the third liquid level h3, on the outside chance that the liquid level falls below the first liquid level h1 and arrives at the third liquid level h3, running of the apparatus on an empty tank can be prevented. Also, since the halt sensor 16 is provided separately from the liquid-level sensor 15, even should the liquid level sensor 15 fail, utilizing of the halt sensor 16 makes it possible to prevent a dangerous empty-tank running state from coming about.

In addition, because the liquid-level sensor 15 is connected to an external part of the atomization tank 11, the influence of local liquid-surface fluctuations in the atomization tank 11 that accompany operation of the ultrasonic vibration elements can be reduced, making it possible to measure accurate liquid levels.

In addition, because the liquid formulation is supplied via the electromagnetic valve from the tank unit 20 arranged above the atomization tank 11, and the liquid formulation can be supplied exploiting gravity, and meanwhile because liquid-formulation supply control can be carried out by only opening-and-closing controlling the electromagnetic valve, a spraying apparatus 1 is afforded that is capable of supplying liquid formulation to the atomization tank 11 more rapidly than by employing the liquid-formulation supply pump 41.

Since the spouting unit 30 is formed by a approximately cylindrical spouting element having predetermined width, depth and height, the generated fine particles are prevented from adhering to the wall surfaces of the spouting element. Further, because a spray port 31 in the form of a slit inclined diagonally upward is furnished along the upper edge of the spouting unit 30, pressure loss during spraying can be controlled to a minimum, wherein even if the pressure for spraying is low, wide-range spraying is possible. Designing in this way affords a spraying apparatus 1 capable of spraying a sufficient volume of fine particles over a broad range even in instances in which the rpm of the blower 13 is low.

In addition, by the atomization tank 11 being anchored to the lower-part base 61, fine particles are produced in the lowest part of the spraying apparatus 1. What is more, by the spouting unit 30 being disposed on the uppermost part upward of the tank unit 20 arranged above the atomization tank 11, the fine particles that are produced ascend from the bottommost part of the apparatus and spout out from the uppermost part. Therefore afforded is a spraying apparatus 1 exploiting the chimney effect to enable the spraying of fine particles over a wide range, even in instances in which the rpm of the blowing element is lowered, lowering the pressure of the blower 13.

The fact that the liquid formulation replenishing port 63e for replenishing the tank unit 20 with liquid formulation is furnished in the recess 63c provided in the top panel of the top component 63 means that replenishing-supply of liquid formulation from above in a high position in the apparatus is possible, which facilitates replenishing-supply of the liquid formulation. Further, because the liquid-formulation supply port 63e is covered by the door-lid 63d during the spraying operation, there is no danger of foreign matter entering into the tank unit 20 interior when the door-lid 63e is closed, affording, moreover, a spraying apparatus with a neat appearance.

The fact that the periphery of the columnar members 62 is covered with the cover member 80 formed by a stainless-steel sheet affords a spraying apparatus 1 that enables the atomizing unit 10, the tank unit 20, etc. to be covered and concealed from the external environment, and that at the same time gives a sleek impression. In addition, since the cover member is formed by a sheetlike component having elasticity, it can be arranged utilizing the elastic force to wrap it onto the periphery of the columnar members, so that even persons unused to the job can easily attach and detach the cover member 80. Furthermore, the fact that the cover member is strong against corrosion by acids, affords a spraying apparatus 1 that enables the utilization of various liquid formulations, and that can be employed in various environments.

By atomizing the chlorous acid aqueous solution utilizing ultrasonic vibration elements, fine particles tiny to a level that can give rise to Brownian motion can be generated. In addition, because the fine particles generated utilizing the chlorous acid aqueous solution are not prone to becoming deactivated even after a long-term elapse of time, the decontaminating effect can continue over a long period of time. In that situation, the fact that the atomization tank 11 and the tank unit 20 are formed from polyethylene terephthalate, which possesses strong properties against chlorous acid, affords a spraying apparatus 1 that does not require carrying out long-term maintenance, and that is capable of being run continuously. Likewise, because the mounting unit 60 is made of stainless steel, it is not susceptible to corrosion, and the component replacement and the like that is attendant on rusting can be avoided, enabling stabilized running over still longer periods of time.

While the embodying modes of the present invention have been described above, the present invention is not limited to these above-described embodying modes. Furthermore, the effects described in embodying modes of the present invention are merely listing of most favorable effects that arise from the present invention; the effects of the present invention are not limited to those described in the embodying modes of the present invention.

In addition, the above-described embodying modes are described in detail for the purpose of explaining the present invention for comprehensibility, and are not necessarily limited to those with all of the described configurations.

Industrial Exploitability

The spraying apparatus of the present invention can be applicable to various spraying devices that spray various types of liquids.

Explanation of Reference Marks

| Explanation of Reference Marks | | | |
|---|---|---|---|
| 1 | Sprayer | | |
| 10 | Atomizing unit | | |
| | 11 | Atomization tank | |
| | | 11a | Inlet |
| | | 11b | Blow port |
| | | 11c | Send-out port |
| | | 11d | Top panel |
| | 12 | Atomization device | |
| | | 12a, b . . . | Ultrasonic vibration elements |
| | 13 | Blower | |
| | 14a, b | Baffle plate | |
| | 15 | Liquid-level sensor | |
| | 16 | Halt sensor | |
| 20 | Tank unit | | |
| 30 | Spouting unit | | |
| | 31 | Spouting element | |
| | 32 | Spray port | |
| 40 | Supply unit | | |
| 50 | Control unit | | |
| 60 | Mounting unit | | |
| | 61 | Lower-part base | |
| | 62 | Columnar member | |
| | 63 | Top member | |
| | 64 | Legs | |
| 70 | Power supply unit | | |
| 80 | Cover member | | |

The invention claimed is:

1. A spraying apparatus comprising:
   an atomization tank enabled for storing a liquid formulation;
   an atomizing device being ultrasonic vibration elements arranged in the atomization tank interior, for atomizing the liquid formulation to generate fine particles;

a blower enabled for maintaining predetermined rpm, for blasting into the atomization tank interior, through a blow port provided in a top panel of the atomization tank, conveyance air that is for conveying the fine particles of the liquid formulation;

a send-out port, provided in the atomization tank, through which the fine particles are sent out together with the conveyance air; and a baffle plate arranged in the atomization tank interior so as to receive liquid columns of the liquid formulation, produced by the ultrasonic vibration elements; wherein the baffle plate is arranged directed toward one widthwise end of the atomization tank, and meanwhile comprises an edge part disposed in the atomization tank spaced apart at a predetermined spacing from a lateral surface along the one widthwise end and a connection part directly connected to an inner side of the top panel of the atomization tank;

the baffle plate is disposed above the ultrasonic vibration elements, and underneath the blow port, in an orientation blocking liquid columns produced by the ultrasonic vibration elements, and conveyance air blasted through the blow port by the blower; and the blow port and the send-out port are provided on an inner surface of the atomization tank and in locations on opposites sides from each other, with the connection part put in between.

* * * * *